US006274119B1

(12) United States Patent
Barrio et al.

(10) Patent No.: US 6,274,119 B1
(45) Date of Patent: Aug. 14, 2001

(54) METHODS FOR LABELING β-AMYLOID PLAQUES AND NEUROFIBRILLARY TANGLES

(75) Inventors: Jorge R. Barrio, Agoura Hills, CA (US); Andrej Petric, Ljubljana (SI); Nagichettiar Satyamurthy; Gary W. Small, both of Los Angeles, CA (US); Gregory M. Cole, Santa Monica; Sung-Cheng Huang, Sherman Oaks, both of CA (US)

(73) Assignee: The Regents of the Univ. of California, Oakland, CA (US)

( * ) Notice: Subject to any disclaimer, the term of this patent is extended or adjusted under 35 U.S.C. 154(b) by 0 days.

(21) Appl. No.: 09/378,662

(22) Filed: Aug. 20, 1999

Related U.S. Application Data

(60) Provisional application No. 60/097,320, filed on Aug. 20, 1998.

(51) Int. Cl.$^7$ .................................................. A61K 51/00

(52) U.S. Cl. ........................................ 424/1.81; 424/1.85

(58) Field of Search ................................ 424/1.85, 1.81, 424/1.89, 1.65, 9.1, 9.3, 9.6

(56) References Cited

U.S. PATENT DOCUMENTS 5,227,308   7/1993  Jameson et al. ...................... 436/172
5,614,502   3/1997  Flotte et al. ............................ 514/34

OTHER PUBLICATIONS

Jacobson, A., "1,1–Dicyano–2–[6–(dimethylamino)naphthalen–2–yl]propene (DDNP): A Solvent Polarity and Viscosity Sensitive Fluorophore for Fluorescence Microsopy", J. Am. Chem. Soc., 1996, vol. 118, No. 2, pp. 5572–5579.
N. Alizadeh–Pasdar and E. C. Y. Li–Chan,"Application of PRODAN Fluorescent Probe to Measure Surface Hydrophobicity of Proteins Interacting with K–carrageenan" The IFT 1999 Annual Meeting, one page, 1999.
Klunk, W., et al., "Development of Small Molecule Probes for the Beta–Amyloid Protein of Alzheimer's Disease", Neurobiology of Aging, vol. 15, No. 6, pp. 691–698, 1994.
Klunk, W., et al., "Chrysamine–G Binding to Alzheimer and Control Brain: Autopsy Study of a New Amyloid Probe", Neurobiology of Aging, vol. 16, No. 4, pp. 541–548, 1993.
Dezutter, et al., "Preparation of $^{99m}$Tc–N$_2$S$_2$ Conjugates of Chrysamiune G, Potential Probes for the Beta–Amyloid Protein of Alzheimer's Disease," Journal of Labelled Compounds and Radiopharmaceuticals J. Labelled Cpd. Radiopharm. 42, (1999) 309–324.

Primary Examiner—Michael G. Hartley
(74) Attorney, Agent, or Firm—Christie, Parker & Hale, LLP

(57) ABSTRACT

A method for labeling β-amyloid plaques and neurofibrillary tangles in vivo and in vitro, comprises contacting a compound of formula (I):

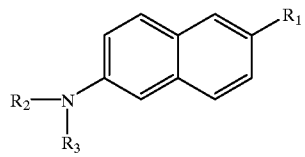

(I)

with mammalian tissue. In formula (I), $R_1$ is selected from the group consisting of —C(O)-alkyl, —C(O)-alkylenyl-$R_4$, —C(O)O-alkyl, —C(O)O-alkylenyl-$R_4$, —C=C(CN)$_2$-alkyl, —C=C(CN)$_2$-alkylenyl-$R_4$ ,

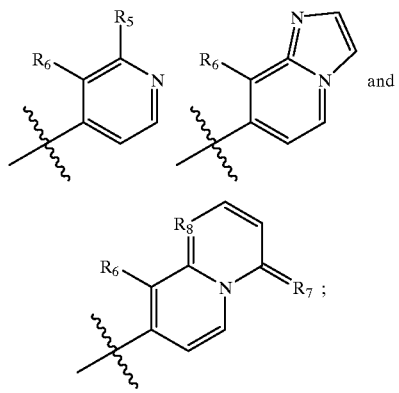

$R_4$ is a radical selected from the group consisting of alkyl, substituted alkyl, aryl and substituted aryl; $R_5$, is a radical selected from the group consisting of —NH$_2$, —OH, —SH, —NH-alkyl, —NHR$_4$, —NH-alkylenyl-$R_4$, —O-alkyl, —O-alkylenyl-$R_4$, —S-alkyl, and —S-alkylenyl-$R_4$; $R_6$ is a radical selected from the group consisting of —CN, —COOH, —C(O)O-alkyl, —C(O)O-alkylenyl-$R_4$, —C(O)-alkyl, —C(O)-alkylenyl-$R_4$, —C(O)-halogen, —C(O)NH , —C(O)NH-alkyl, —C(O)NH-alkylenyl-$R_4$; $R_7$ is a radical selected from the group consisting of O, NH, and S; and $R_8$ is N, O or S. $R_2$ and $R_3$ are each independently selected from the group consisting of alkyl and alkylenyl-$R_{10}$, wherein $R_{10}$ is selected from the group consisting of —OH, —OTs, halogen, spiperone, spiperone ketal and spiperone-3-yl. Alternatively, $R_2$ and $R_3$ together form a heterocyclic ring, optionally substituted with at least one radical selected from the group consisting of alkyl, alkoxy, OH, OTs, halogen, alkylenyl-$R_{10}$, carbonyl, spiperone, spiperone ketal and spiperone-3-yl. In the compounds of formula (I), one or more of the hydrogen, halogen or carbon atoms can, optionally, be replaced with a radiolabel.

25 Claims, 5 Drawing Sheets

(4 of 5 Drawing Sheet(s) Filed in Color)

OTHER PUBLICATIONS

Griffiths, P.D., et al., "Receptor Changes in the Neocortex of Post–Mortem Tissue in Parkinson's Disease and Alzheimer's Disease", Dementia, vol. 3, (1992) pp. 239–246.

Han, et al., "Technetium Complexes for the Quantitation of Brain Amyloid," J. Am. Chem. Soc. 1996, 118, 4506–4507.

Huang, et al., "Neuroreceptor Assay with Positron Emission Tomography: Equilibrium Versus Dynamic Approaches," Journal of Cerebral Blood Flow and Metabolism (1986) 6:515–521.

Imamura, et al., "Regional Cerebral Glucose Metabolism in Dementia with Lewy Bodies and Alzheimer's Disease: a Comparative Study Using Positron Emission Tomography," Neuroscience Letters 235 (1997) 49–52.

Klunk, et al., "Development of Small Molecule Probes for the Beta–Amyloid Protein of Alzheimer's Disease," Neurobiology of Aging, vol. 15, No. 6, (1994) pp. 691–698.

Majocha, et al., "Development of a Monoclonal Antibody Specific for β/A4 Amyloid in Alzheimer's Disease Brain for Application to In Vivo Imaging of Amyloid Angiopathy," The Journal of Nuclear Medicine, vol. 33, No. 12, Dec. 1992, pp. 2184–2189.

Merlini, et al., "Interaction of the Anthracycline 4'–iodo–4'–deoxydoxorubicin with Amyloid Fibrils: Inhibition of Amyloidogenesis," Proc. Natl. Acad. Sci. USA, vol. 92, Mar. 1995, pp. 2959–2963.

Mielke, et al., "Regional Cerebral Glucose Metabolism and Postmortem Pathology in Alzheimer's Disease," Acta Neuropathol (1996) 91:174–179.

Moryś, et al., "The Second Layer Neurones of the Entorhinal Cortex and the Perforant Path in Physiological Ageing and Alzheimer's Disease," Acta Neurobiol. Exp. (1994) 54:47–53.

Naiki, et al., "Fluorometric Determination of Amyloid Fibrils in Vitro Using the Fluorescent Dye, Thioflavine T," Analytical Biochemistry 177, (1989) 244–249.

Price, et al., "Tangles and Plaques in Nondemented Aging and "Preclinical" Alzheimer's Disease," Ann Neurol (1999) 45:358–368.

Saito, et al., "Vector–mediated Delivery of $^{125}$I–Labeled β–amyloid Peptide Aβ$^{1-40}$ Through the Blood–brain Barrier and Binding to Alzheimer Disease Amyloid of the Aβ$^{1-40}$/Vector Complex," Proc. Natl. Acad. Sci. USA, vol. 92, Oct. 1995, pp. 10227–10231.

Salmon, et al., "Differential Diagnosis of (Alzheimer's) Disease with PET," The Journal of Nuclear Medicine, vol. 35, No. 3, Mar. (1994) pp. 391–398.

Tubis, et al., "The Preparation and Use of Radioiodinated Congo Red in Detecting Amyloidosis," Journal of the American Pharmaceutical Association, vol. 49, No. 7, Jul. 1960, pp. 422–425.

METHODS FOR LABELING β-AMYLOID PLAQUES AND NEUROFIBRILLARY TANGLES

CROSS-REFERENCE TO RELATED APPLICATION

This application claims priority of U.S. Provisional Patent Application No. 60/097,320, filed Aug. 20, 1998, the entire disclosure of which is incorporated herein by reference.

ACKNOWLEDGEMENT OF GOVERNMENT SUPPORT

This invention was made with government support under Grant No. DE-FC0387-ER60615, awarded by the Department of Energy. The government has certain rights in the invention.

BACKGROUND OF THE INVENTION

Alzheimer's disease affects approximately 20 to 40% of the population over 80 years of age, the fastest growing age group in the United States and other post-industrial countries. Common features in the brain of patients with Alzheimer's disease include the presence of abundant intraneuronal neurofibrillary tangles (NFTs) and extracellular amyloid rich β-amyloid plaques. NFTs are cytoskeletal pathologies largely composed of aggregates of hyperphosphorylated tau proteins assembled into periodically restricted amyloid fibers called paired helical filaments. The major component of amyloid plaques is a peptide, a small 39–43 aminoacid long β-amyloid peptide that is generated from the cleavage of a larger amyloid precursor protein. However, except for diffuse plaques formed almost exclusively of B-amyloid peptides, amyloid plaques are complex lesions containing numerous associated cellular products. Mutations causing increased production of the 42 amino acid form of this peptide have been genetically linked to autosomal dominant familial forms of Alzheimer's diseases. Deposits of β-amyloid occur very early in the disease process, long before clinical symptoms develop. Because these mutations appear to be pathogenic and cause Alzheimer's diseases in transgenic mice, β-amyloids are widely believed to play a causal role in the disease. Whether or not amyloid deposits are causal, they are certainly a key part of the diagnosis. Further, because amyloid plaques occur early in the disease, the ability to image deposits would provide a convenient marker for early diagnosis and prevention of the disease as well as a method for monitoring the effectiveness of therapeutic regimens.

Alzheimer's disease is currently definitively diagnosed by taking sections from postmortem brain and quantifying the density of neocortical amyloid deposits. Unfortunately, current techniques for detecting amyloid deposits and/or NFTs require postmortem or biopsy analysis. For example, thioflavin fluorescent-labeling of amyloid in brain sections in vitro is currently a widely-used method for evaluation of the brain. Another potential amyloid probe, Chrysamine-G, a congo red derivative, has also been developed. Congo red is a charged molecule and thus lacks sufficient hydrophobicity for diffusion through the blood brain barrier and is therefore not useful as an in vivo label. See Klunk et al, Neurobiology of Aging, 16:541–548 (1995), and PCT Publication No. WO 96/34853. Chrysamine G enters the blood brain barrier better than Congo red, but its ability to label amyloid plaques in Alzheimer's brain appears weak. See for example, H. Han, C-G Cho and P. T. Lansbury, Jr *J. Am. Chem. Soc.* 118, 4506 (1996); N. A. Dezutter et al, *J. Label. Compd. Radiopharm.* 42, 309 (1999). Similarly, earlier attempts to use monoclonal antibodies as probes for in-vivo imaging of β-amyloid were hampered by their limited ability to cross the blood brain barrier. See R. E. Majocha et al, *J. Nucl. Med.* 33, 2184 (1992). More recently, the use of monobiotinylated conjugates of 1251 -Aβ1-40 with permeability through the blood brain barrier has also been proposed (See Y. Saito et al., *Proc. Natl. Acad. Sci. USA* 22, 2288 (1991)), but its ability to label β-amyloid plaques and/or NFTs in vivo has not yet been demonstrated. Quantitation of the deposits in vivo is not yet possible with the currently available probes. Accordingly, a need exists for a convenient marker for early diagnosis of Alzheimer's disease.

In vivo, non invasive determination of regional cerebral glucose metabolic rates (rCMRGl) with positron emission tomography (PET) has been an important tool in the assessment of brain function in Alzheimer's disease patients. Numerous studies using 2-[F-18]fluoro-2-deoxy-D-glucose (FDG) have demonstrated a characteristic metabolic pattern of hypometabolism in temporoparietal and frontal association areas. A few of these studies have compared rCMRGl with postmortem regional neuronal pathology. These results and the uncertainties of the Alzheimer's disease pathogenic cascade highlight the importance of assessing amyloid and neurofibril deposition in vivo, non-invasively in these patients.

SUMMARY OF THE INVENTION

The present invention provides methods for labeling structures, including β-amyloid plaques and neurofibrillary tangles, in vivo and in vitro, and comprises contacting a compound of formula (I):

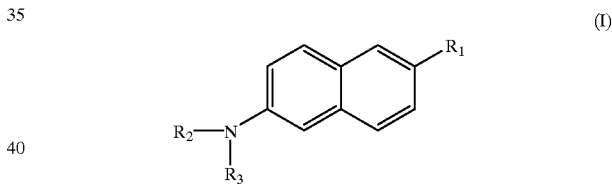

(I)

with mammalian tissue. In formula (I), $R_1$ is selected from the group consisting of —C(O)-alkyl, —C(O)-alkylenyl-$R_4$, —C(O)O-alkyl, —C(O)O-alkylenyl-$R_4$, —C=C(CN)$_2$-alkyl, —C=C(CN)$_2$-alkylenyl-$R_4$,

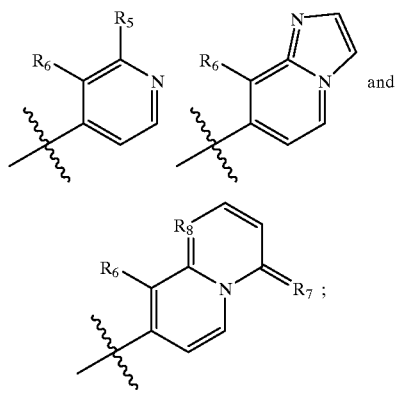

and $R_4$ is a radical selected from the group consisting of alkyl, substituted alkyl, aryl and substituted aryl; $R_5$ is a radical selected from the group consisting of —NH$_2$, —OH, —SH, —NH-alkyl, —NHR$_4$, —NH-alkylenyl-R$_4$, —O-alkyl, —O-alkylenyl-R$_4$, —S-alkyl, and —S-alkylenyl-R$_4$; R$_6$ is a radical selected from the group consisting of —CN, —COOH, —C(O)O-alkyl, —C(O)O-alkylenyl-R$_4$, —C(O)-alkyl, —C(O)-alkylenyl-R$_4$, —C(O)-halogen, —C(O)NH, —C(O)NH$_2$-alkyl, —C(O)NH-alkylenyl-R$_4$; R$_7$ is a radical selected from the group consisting of O, NH, and S; and R$_8$ is N, O or S.

In formula (I), R$_2$ and R$_3$ are each independently selected from the group consisting of alkyl and alkylenyl-R$_{10}$, wherein R$_{10}$ is selected from the group consisting of —OH, —OTs, halogen, spiperone, spiperone ketal and spiperone-3-yl. Alternatively, R$_2$ and R$_3$ together form a heterocyclic ring, optionally substituted with at least one radical selected from the group consisting of alkyl, alkoxy, OH, OTs, halogen, alkylenyl-R$_{10}$, carbonyl, spiperone, spiperone ketal and spiperone-3-yl. In the compounds of formula (I), one or more of the hydrogen, halogen or carbon atoms can, optionally, be replaced with a radiolabel.

For in vitro detection of β-amyloid plaques and neurofibrillary tangles in brain tissue, the plaques are labeled, and the brain tissue is then observed with a fluorescence microscope. For in vivo detection, the β-amyloid plaques and neurofibrillary tangles in brain tissue are labeled, preferably by injection of a solution containing a radiolabeled compound of formula (I). The locations of the labeled β-amyloid plaques and neurofibrillary tangles are then observed by any method capable of detecting and depicting the distribution of the radiolabeled compound within the body.

According to the methods of the invention, amyloid deposits in cryostat and paraffin sections of Alzheimer-diseased (AD) brain tissue are labeled with a level of sensitivity similar to thioflavin S. Use of the present invention, however, has several advantages over using thioflavin S. Namely, no pretreatments are required. Moreover, unlike with thioflavin S, the methods work with minimal washing and without formalin or paraformaldehyde fixation or differentiation of tissue. Additionally, stock solution can be kept in the freezer for six months and still produce acceptable results at 1/100 to 1/1,000 dilutions, eliminating the need to make the stock up fresh, as is required for thioflavin S labeling.

Systemically injected compositions according to the invention readily penetrate the blood brain barrier and label amyloid deposits and neurofibrillary tangles demonstrating the ability of the present compositions to act as an in vivo imaging probe. The methods of the invention achieve in vivo labeling and detection of β-amyloid plaques and neurofibrillary tangles in the brain of a living patient. The methods of the invention not only permit detection of Alzheimer's disease, but also provide a way for physicians to monitor the progress of patients undergoing treatment for the disease. Thus, physicians can better determine whether a particular treatment method is successful and worthwhile.

In still another embodiment, the invention is directed to a composition comprising a compound of formula (I):

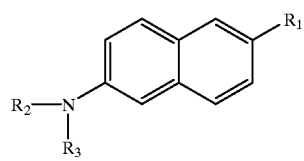

(I)

R$_1$ is selected from the group consisting of —C(O)-alkyl, —C(O)-alkylenyl-R$_4$, —C(O)O-alkyl, —C(O)O-alkylenyl-R$_4$, —C=C(CN)$_2$-alkyl, —C=C(CN)$_2$-alkylenyl-R$_4$,

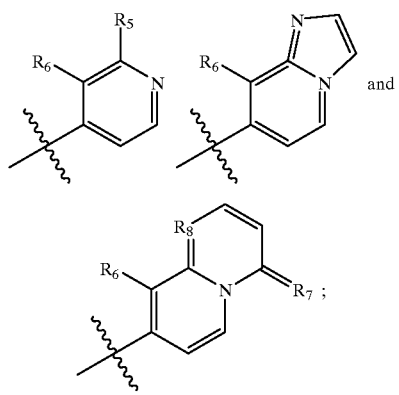

and

R$_4$ is a radical selected from the group consisting of alkyl, substituted alkyl, aryl and substituted aryl; R$_5$ is a radical selected from the group consisting of —NH$_2$, —OH, —SH, —NH-alkyl, —NHR$_4$, —NH-alkylenyl-R$_4$, —O-alkyl, —O-alkylenyl-R$_4$, —S-alkyl, and —S-alkylenyl-R$_4$; R$_6$ is a radical selected from the group consisting of —CN, —COOH, —C(O)O-alkyl, —C(O)O-alkylenyl-R$_4$, —C(O)-alkyl, —C(O)-alkylenyl-R$_4$, —C(O)-halogen, —C(O)NH$_2$, —C(O)NH-alkyl, —C(O)NH-alkylenyl-R$_4$; R$_7$ is a radical selected from the group consisting of O, NH, and S; R$_8$ is N, O or S; R$_2$ is selected from the group consisting of alkyl and alkylenyl-R$_5$ and R$_3$ is alkylenyl-R$_5$, and R$_5$ is selected from the group consisting of —OH, —OTs, halogen, spiperone, spiperone ketal, and spiperone-3-yl, or R$_2$ and R$_3$ together form a heterocyclic ring, optionally substituted with at least one radical selected from the group consisting of alkyl, alkoxy, OH, OTs, halogen, alkylenyl-R$_5$, carbonyl, spiperone, spiperone ketal and spiperone-3-yl. One or more of the hydrogen, halogen or carbon atoms can optionally be replaced with a radiolabel.

The invention is more preferably related to a composition comprising a compound of formula (II):

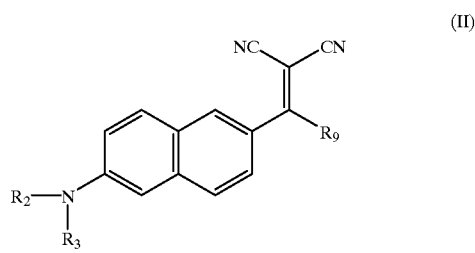

(II)

R$_2$ is selected from the group consisting of alkyl and alkylenyl-R$_{10}$ and R$_3$ is alkylenyl-R$_{10}$, wherein R$_{10}$ is selected from the group consisting of —OH, —OTs, halogen, spiperone, spiperone ketal and spiperone-3-yl, or R$_2$ and R$_3$ together form a heterocyclic ring, optionally substituted with at least one radical selected from the group consisting of alkyl, alkoxy, OH, OTs, halogen, alkylenyl-R$_{10}$, carbonyl, spiperone, spiperone ketal and spiperone-3-yl, and R$_9$ is an alkyl, aryl or substituted aryl group, and to pharmaceutically acceptable salts and solvates thereof. One or more of the hydrogen, halogen or carbon atoms can optionally be replaced with a radiolabel.

DESCRIPTION OF THE DRAWINGS

The file of this application contains at least one drawing executed in color. Copies of this patent with color drawings (s) will be provided by the Patent an Trademark Office upon request and payment of the necessary fee.

These and other features and advantages of the present invention will be better understood by reference to the following detailed description when considered in conjunction with the accompanying drawings wherein:

FIG. 2B demonstrates in vivo DDNP fluorescently labeled amyloid at the tip of the need track (X100).

DETAILED DESCRIPTION OF THE INVENTION

Figure 1A:
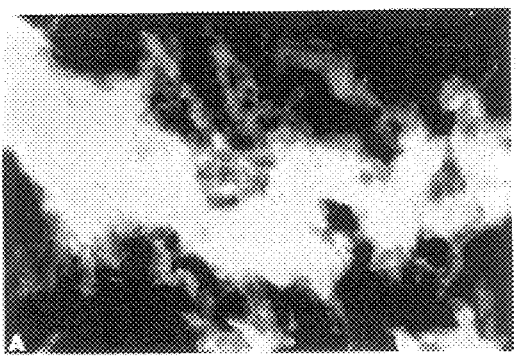
FIG. 1A shows 2-(1,1-dicyanopropen-2-yl)-6-dimethylaminonaphthalene (DDNP) fluorescence (ex 490 nm, em 520–530 nm) of amyloid plaques labeled in the cortex of the brain of an Alzheimer's disease patient (X400).
Figure 1B:
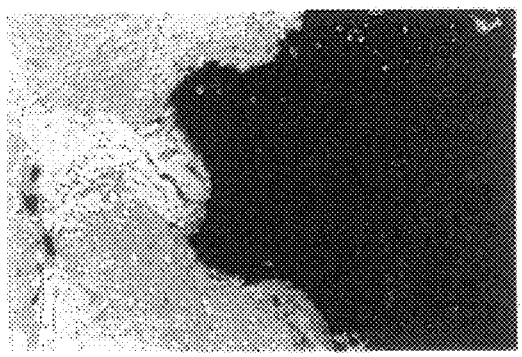
FIG. 1B shows strong DDNP labeling of plaques and weak DDNP labeling of tangles in the cortex of the brain of an Alzheimer's disease patient (X640).
Figure 1C:
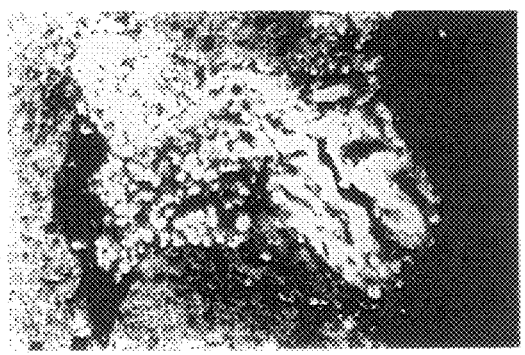
FIG. 1C shows DDNP labeling of a single, large plaque with an amyloid core in human brain (X640).
Figure 1D:
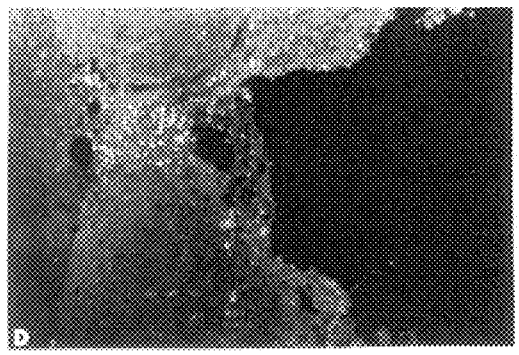
FIG. 1D shows DDNP labeling of a plaque in agent Tg2576 HuAPPsw transgenic mouse brain (X500).
Figure 1E:
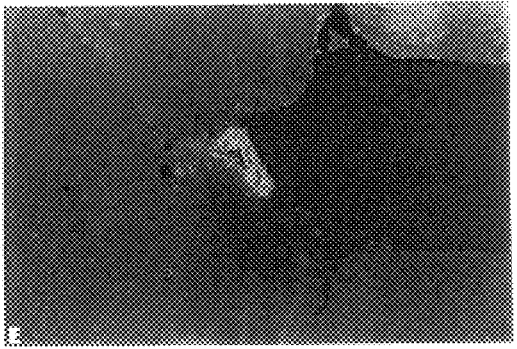
FIG. 1E shows Thioflavin S labeling of a cored plaque in Alzheimer's disease human brain (X640).
Figure 1F:
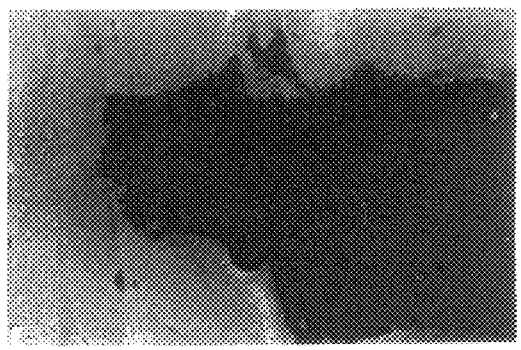
FIG. 1F shows 4G8 antibody labeling amyloid β-protein of a slice of the same human brain shown in FIG. 1E (X640).
Figure 2A:
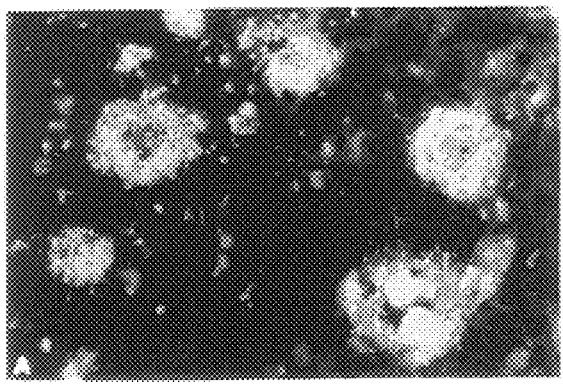
FIG. 2A shows labeling of amyloid injected into rat brain, where an aliquot of β-amyloid 1-40 was allowed to aggregate for 8 days at 37° C., dried onto a gelatin coated slide, and labeled with DDNP, demonstrating fibrillar fluorescence consistent with amyloid.
Figure 2B:
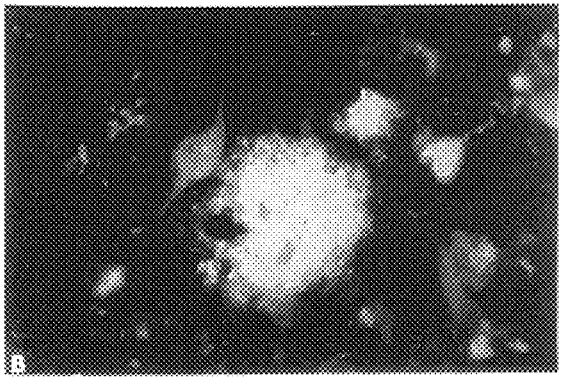
FIG. 2B shows labeling of amyloid injected into rat brain, where 8 days after unilateral stereotaxic injection of 3 μg of aggregated β-amyloid 1-40 into rat cortex, the rats were injected with 100 μL of 640 μM DDNP into the carotid artery, anesthetized, and sacrificed by perfusion after 20 minutes and the brains were cryosectioned and examined for fluoroescence.
Figure 2C:
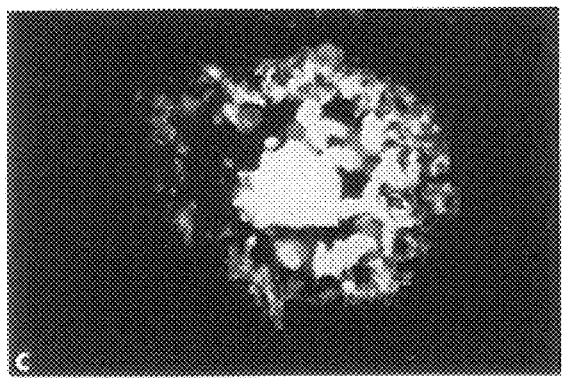
FIG. 2C shows a high power view of the in vivo DDNP labeled material of FIG. 2B (X200).
Figure 2D:
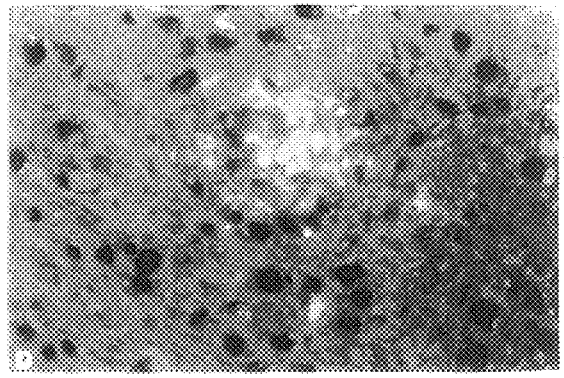
FIG. 2D depicts how formic acid treatment of a section through the injection site removes fluorescent labeling (X100).
Figure 2E:
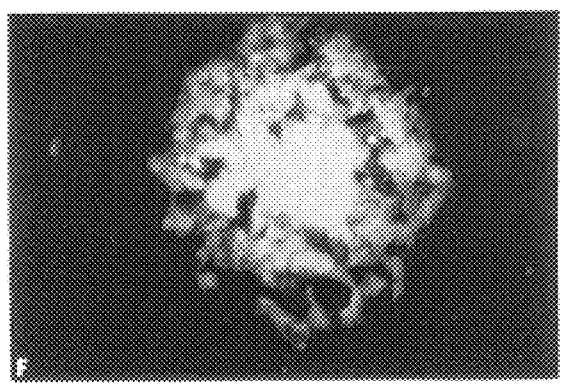
FIG. 2E demonstrates that DDNP labeling is weak contralateral to the amyloid injection site, where no amyloid is present (X200).

The present invention is directed to methods for labeling structures such as β-amyloid plaques and neurofibrillary tangles in vivo and in vitro. The methods all involve contacting a compound of formula (I):

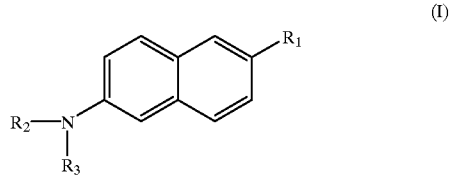

with mammalian tissue. In formula (I), $R_1$ is selected from the group consisting of —C(O)-alkyl, —C(O)-alkylenyl-$R_4$, —C(O)O-alkyl, —C(O)O-alkylenyl-$R_4$ —C=C(CN)$_2$-alkyl, —C=C(CN)$_2$-alkylenyl-$R_4$

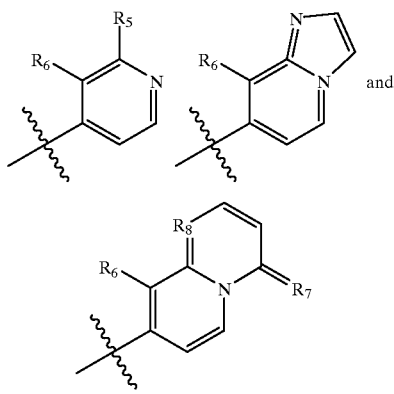

$R_4$ is a radical selected from the group consisting of alkyl, substituted alkyl, aryl and substituted aryl. $R_5$ is a radical selected from the group consisting of —NH$_2$, —$_2$OH, —SH, —NH-alkyl, —NHR$_4$, —NH-alkylenyl-$R_4$, —O-alkyl, —O-alkylenyl-$R_4$, —S-alkyl, and —S-alkylenyl-$R_4$. $R_6$ is a radical selected from the group consisting of —CN, —COOH, —C(O)O-alkyl, —C(O)O-alkylenyl-$R_4$, —C(O)-alkyl, —C(O)-alkylenyl-$R_4$, C(O)-halogen, —C(O)NH$_2$, —C(O)NH-alkyl, —C(O)NH-alkylenyl-$R_4$. $R_7$ is a radical selected from the group consisting of O, NH, and S. $R_8$ is N, O or S.

In formula (I), $R_2$ and $R_3$ are each independently selected from the group consisting of alkyl and alkylenyl-$R_{10}$, wherein $R_{10}$ is selected from the group consisting of —OH, —OTs, halogen, spiperone, spiperone ketal and spiperone-3-yl. Alternatively, $R_2$ and $R_3$ together form a heterocyclic ring, optionally substituted with at least one radical selected from the group consisting of alkyl, alkoxy, OH, OTs, halogen, alkylenyl-$R_{10}$, carbonyl, spiperone, spiperone ketal and spiperone-3-yl. In the compounds of formula (I), one or more of the hydrogen, halogen or carbon atoms may optionally be replaced with a radiolabel.

In a preferred embodiment, the methods of the invention involve contacting a compound of formula (II):

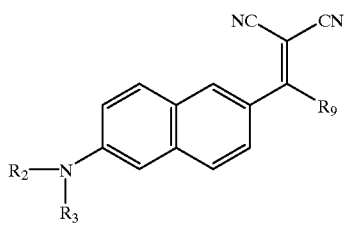

(II)

with mammalian tissue. In formula (II), $R_2$ and $R_3$ are as defined above, and $R_9$ is an alkyl, aryl or substituted aryl group.

As used herein, the term "alkyl" refers to a straight or branched chain monovalent radical of saturated carbon atoms and hydrogen atoms, such as methyl, ethyl, propyl, isopropyl, butyl, isobutyl, t-butyl, pentyl, and hexyl. The term "alkylenyl" refers to a divalent analog of an alkyl group, i.e., methylenyl (—CH$_2$—), ethylenyl (—CH$_2$CH$_2$—), etc. The term "aryl" refers to a mono- or polycyclic substituted or unsubstituted aromatic ring.

As used herein, the term "lower alkyl" refers to a straight or branched chain monovalent radical having from one to four saturated carbon atoms and hydrogen atoms, such as methyl, ethyl, propyl, isopropyl, butyl, isobutyl, and t-butyl.

As used herein, the term "heterocyclic ring" refers to a non-aromatic, monocyclic or bicyclic radical containing 3, 4, 5, 6, 7, 8, 9, 10, 11, or 12 ring atoms, each of which is saturated or unsaturated, including 1, 2, 3, 4, or 5 heteroatoms selected from nitrogen, oxygen and sulfur. Nonlimiting examples include aziridine, azetidine, pyrrolidine, piperidine, piperizine and derivatives thereof. Preferably, these heterocyclic rings are substituted with alkyl groups or substituted alkyl groups, for example, alkyl groups having substituents such as those defined for $R_4$ above.

For the compounds of formula (I) and formula (II), preferably $R_2$ and $R_3$ are each independently alkyl, more preferably lower alkyl. For the compounds of formula (II), preferably $R_9$ is lower alkyl, more preferably methyl or ethyl, aryl and substituted aryl. Particularly preferred compounds for use in connection with the invention are 2-(1,1-dicyanopropen-2-yl)-6-dimethylaminonaphthalene (DDNP) and 2-(1,1-dicyanopropen-2-yl)-6-(ethyl)(methyl)(amino)-naphthalene, both of which can be optionally radiolabeled. Another preferred compound, particularly for use in vivo, is 2-(1.1-dicyanopropen-2-yl)-6-(2-[$^{18}$F]-fluoroethyl)-methylamino)-naphthalene ([F-18]FDDNP).

The present invention is also directed to methods for detecting structures, such as β-amyloid plaques and neurofibrillary tangles in vitro and in vivo. The term "structures" refers to aggregates of biological materials containing peptides and other cellular materials that may occur as part of a disease pathology. The term "peptides" includes proteins.

The compounds described above have fluorescent activity in the range of about 470 to 610 nm. In one application, the present invention labels β-amyloid plaques and neurofibrillary tangles in brain tissue. Accordingly, for in vitro detection Alzheimer's disease, the compounds are contacted with brain tissue, and the brain tissue observed with a fluorescence microscope.

For in vivo detection, preferably the compounds are radiolabeled. A preferred radiolabel is $^{18}$F, which has a half-life of approximately two hours for position emission tomography (PET). Another radiolabel is radioiodine, for example, $^{123}$I for use with single photon emission computed tomography (SPECT). Alternatively, other radiolabels are used, such as $^{11}$C, $^{13}$N and $^{15}$O, although these radiolabels are less desirable due to their relatively short half-lives. Any atom in the compound can be replaced with a suitable radiolabel. Radiolabeling can be achieved by any method known to those skilled in the art. For example, dry [F-18] fluoride ion [$^{18}$O(p,n)$^{18}$F] in K$_2$CO$_3$ (0.75 mg) and Kryptofix 2.2.2™ (19 mg) are added to a solution of the compound of formula (I) or formula (II) (4 mg in 1 mL CH$_3$CN). The mixture is heated in an oil bath at 85° C. for about 10 to 40 minutes. After cooling and dilution with water, the radiolabeled product can be purified by preparative HPLC. Kryptofix 2.2.2™ is a crown ether, available from Aldrich Chemical Co. (Milwaukee, Wis.).

A solution containing the radiolabeled compound is then injected into the patient. As used herein, the term "patient" refers to any mammal, including humans, rats, mice, dogs and cats. Neuroanatomical regions can be determined manually using MRI scans, for example, using a Tela magnet, and then on amyloid-PET (positron emission tomography) and FDG-PET (fluorodeoxyglucose-PET) by coregistration of the MRI scans. PET has current resolution of 2 to 3 min, a dynamic determination of radiolabeled compound deposition in the brain, and permits detection of abnormal areas.

By the above-described methods, diseases characterized by the accumulation of β-amyloid plaques and neurofibrillary tangles such as Alzheimer's disease and other diseases associated with brain deterioration, can be detected.

EXAMPLES

Example 1

The following compositions according to the invention were prepared. NMR spectra were obtained on Bruker AM 360 WB or DPX 300 Spectrometers. $^1$H chemical shifts are reported in ppm downfield from TMS as an internal standard. $^{19}$F chemical shifts are reported relative to external fluorotrichloromethane. Deuteriochloroform was used as the solvent unless stated otherwise. Melting points were determined on an Electrothermal Melting Point Apparatus and are uncorrected. Elemental analyses were performed by Galbraith Laboratories, Inc., Knoxville, Tenn. or Ms. Metka Kastelic at the Faculty of Chemistry and Chemical Technology, University of Ljubljana. Radial chromatography was performed on Chromatotron (Harrison Research, 840 Moana Court, Palo Alto, Calif. 94306). The rotors were prepared as recommended by Harrison Research using E. Merck Silica Gel (Cat. No. 7749-3). HPLC was performed on an Allitech Econosil C-18 5 μm, 4.6×250 mm column using a 40:60:2 mix of water:acetonitrile:triethyl amine as the solvent. UV detection at 254 nm was used. Solvents and reagents were from Fisher, Aldrich or Fluka and were used as received unless noted otherwise.

Example 1(a)—Preparation of 2-(1,1-dicyanopropen-2-yl)-6-dimethylaminonaphthalene (DDNP)

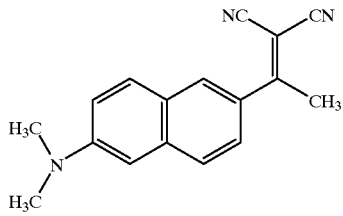

To a solution of 5.26 g (117 mmol) of dimethylamine in 29 mL of freshly distilled hexamethylphosphoric triamide (HMPT) were added 31 mL of dry toluene and 780 mg (112 mmol) of Li in small pieces. The mixture was stirred under argon at room temperature for 1.5 hours. 2-Acetyl-6-methoxynaphthalene was prepared as described in Arsenijevic et al., Org. Synth. Coll. 1988, 6:34–36, the disclosure of which is incorporated herein by reference. 2-Acetyl-6-methoxynaphthalene (5.57 g, 27.8 mmol) was added in one portion, and stirring was continued for 20 hours. The mixture was cooled in an ice-water bath and poured into a cold water/ethyl acetate mixture (300 mL each). After thorough mixing, the layers were separated, and the water layer was extracted twice with 225 mL of ethyl acetate. Organic extracts were combined, dried, and evaporated to give a yellow solid. Recrystallization from ethanol afforded 3.67 g (64%) of 2-acetyl-6-(dimethylamino)naphthalene (ADMAN) as a yellow solid, melting at 153.5–155° C.: $^1$H NMR (CDCl$_3$, TMS) δ2.67 (s, 3H, COCH$_3$), 3.15 (s, 6H, N(CH$_3$)$_2$), 6.87 (d, 1H, H-5), 7.17 (dd, 1H, H-7), 7.63 (d, 1H, H-4), 7.80 (d, 1H, H-8), 7.92 (dd, 1H, H-3), 8.32 (bs, 1H, H-1). $J_{1,3}$=2.3 Hz, $J_{5,7}$=2.4 Hz, $J_{7,8}$=9.3 Hz. MS (M$^+$) 213: found: 213. Anal. Calcd for C$_4$H$_{15}$NO: C, 78.84: H, 7.09; N, 6.57. Found C, 78.96; H, 7.10; N, 6.45.

A mixture of malonitrile (436 mg, 6.6 mmol) and ADMAN (1.278 g, 6.6 mmol) was heated to 110° C. in 20 mL of pyridine for 19 hours. After cooling, the remaining red solid was dissolved in 100 mL of methylene chloride, adsorbed onto 10 g of flash silica get (230–400 mesh) and chromatographed with toluene. Appropriate fractions were combined and evaporated to give 1.12 g (72%) of 2-(1,1-dicyanopropen-2-yl)-6-dimethylaminonaphthalene (DDNP). Recrystallization from benzene-hexane gave red needles melting at 154.5–155° C.: $^1$H NMR (CDCl$_3$, TMS) δ2.69 (s, 3H, CH$_3$), 3.11 (s, 6H, N(CH$_3$)$_2$), 6.85 (d, 1H, H-5), 7.18 (dd, 1H, H-7), 7.56 (dd, 1H, H-3), 7.66 (d, 1H, H-4), 7.76 (d, 1H, H-8), 8.02 (d, 1H, H-1). $J_{1,3}$=2.04 Hz, $J_{3,4}$=9.13 Hz, $J_{5,7}$=2.5 Hz. $J_{7,8}$=9.11 Hz. IR (CHCl$_3$) 2250 cm$^{-1}$ (CN stretching). MS (M$^+$) 261: found: 262. Anal. Calcd for C$_{17}$H$_{15}$N$_3$: C, 78.13: H, 5.79; N, 18.08. Found C, 78.17; H, 5.68; N, 17.91.

Example 1(b)—Preparation of 2-(1-{6[ethyl-(2-{8-[4-(4-fluorophenyl)-4-oxobutyl]-4-oxo-1-phenyl-1,3,8-triazaspiro[4.5]dec-3-yl}ethyl)-amino]-2-naphthyl}ethylidene)malononitrile

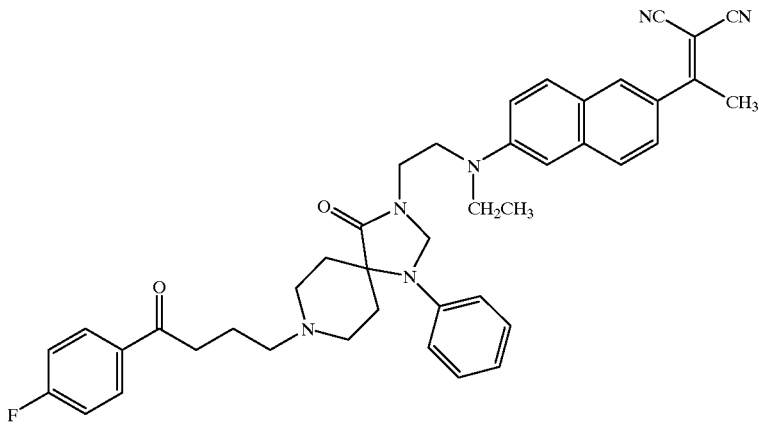

In a 3 L two-neck round bottom flask, equipped with a reflux condenser and a dropping funnel, 2 L of hydrochloric acid (d=1.16) were stirred and heated to boiling. A solution of 6.06 g (30.3 mmol) of 1-(6-methoxy-2-naphthyl)-1-ethanone (prepared as described in Arsenijevic et al., Org. Synth. Coll. 6:34 (1988), the disclosure of which is incorporated herein by reference) in a minimum amount of dichloromethane was added, and the mixture was stirred and heated at reflux for 2 hours. The hot solution was filtered through a mineral wool plug to remove oily residue. The solid that separated after cooling was filtered on a glass frit and dissolved in 130 mL of ethyl acetate. The solution was washed with brine, dried with anhydrous magnesium sulfate and evaporated to give 5 g (89%) of 1-(6-hydroxy-2-naphthyl)-1-ethanone.

A mixture of 1-(6-hydroxy-2-naphthyl)ethanone (744 mg, 3.92 mmol), sodium hydrogen sulfate(IV) (1.66 g, 16 mmol), 2-ethylaminoethanol (2 mL) and water (5 mL) was heated in a steel bomb at 130–140° C. for 3 days. After cooling, the mixture was distributed between water and ethyl acetate, and the organic layer was washed with brine, dried and evaporated. The residue was dissolved in acetone and loaded onto a 4 mm dry silica plate for radial chromatography. The plate was eluted with a 1:1 mixture of petroleum ether and ethyl acetate. Appropriate fractions were collected and evaporated to give 125 mg (12%)of 1-{6-[ethyl-(2-hydroxylethyl)-amino]-2-naphthyl}ethanone.

A solution of 1-{6-[ethyl-(2-hydroxylethyl)-amino]-2-naphthyl}ethanone (125 mg, 0.486 mmol) in pyridine (3.5 mL) was cooled to −15° C. and p-toluenesulfonic anhydride (252 mg, 0.81 mmol) was added with stirring under argon. The reaction mixture was allowed to slowly warm up to the room temperature, and stirring was continued for 24 hours. Because TLC (silica, 10% ethyl acetate in petroleum ether) revealed that the starting material was still present, more p-toluenesulphonic anhydride (252 mg, 0.81 mmol) was added, and stirring was continued for an additional 24 hours. The mixture was then cooled in an ice-water bath and distributed between brine and ether. The organic layer was dried and evaporated to leave an oily residue. The product, 6-acetyl-2-(ethyl-2-[(4-methylphenyl)-sulfonyloxy]-ethylamino)-naphthalene, was isolated by radial chromatography (1 mm silica, dichloromethane) in 30% yield. HRMS calcd. for $C_{23}H_{24}NO_4S$:411.1504. Found: 411.1514. $^1$H NMR δ1.25 (t, 3H, $CH_2\underline{CH_3}$), 2.33 (s, 3H, Ph—$\underline{CH_3}$), 2.67 (s, 3H, $COCH_3$), 3.49 (q, 2H, $\underline{CH_2}CH_3$ ), 3.75 (t, 2H, N $\underline{CH_2}CH_2O$), 4.25 (t, 2H, $CH_2\underline{CH_2}O$), 6.97 (d, 1H, 5-H), 7.01 (dd, 1H, 7-H), 7.18 and 7.20 (d, 2H, 3'-H, 5'-H), 7.56 (d, 1H, 4-H), 7.69 and 7.72 (d, 2H, 2'-H, 6'-H), 7.75 (d, 1H, 8-H), 7.93 (dd, 1H, 3-H), 8.29 (d, 1H, 1-H). $J_{1,3}$=1.6 Hz, $J_{2',6}=J_{3',5}$=8.5 Hz, $J_{7,5}$=2.5 Hz, $J_{7,8}$=9.2 Hz, $J_{3,4}$=8.7 Hz, $J_{(CH2CH3)}$=7.1 Hz, $J_{(NCH2CHH2O)}$=6.2 Hz.

To a solution of sodium hydroxide (1 g) and tetra-n-butylammonium hydrogensulfate (VI) (50 mg, 0.15 mmol) in water (2 mL), spiperone ketal (8-3 [2-(4-fluorophenyl)-1,3-dioxolan-2-yl]propyl-1-phenyl-1,3,8-triazaspiro[4.5] decan-4-one (which can be prepared as described in U.S. Pat. No. 3,839,342, Chem Abstr. 82:43416, and Kiesewetter et al., Appl. Radiat. Isot. 37:1181 (1986), the disclosures of which are incorporated herein by reference) (15 mg, 0.034 mmol) was added and vigorously stirred. After 10 minutes, a solution of 6-acetyl-2-(ethyl-2-[(4-methylphenyl)-sulfonyloxy-ethylamino)-naphthalene (12 mg, 0.03 mmol) in toluene (3 mL) was added, and the reaction mixture was stirred and heated at 90° C. for 1 hour. After cooling, the reaction mixture was distributed between water and dichloromethane, and the organic layer was washed with brine, dried and evaporated to leave an oily residue. Radial chromatography (1 mm silica, 2% methanol in dichlormethane) yielded 5 mg (25%) of 1-[6-(ethyl-2-[(8-3-[2-(4-fluorophenyl)-1,3-dioxolan-2-yl]-propyl-4-phenyl-2,4,8-triazaspiro[4.5]dec-1-en-1-yl)-oxy]-ethylamino)-2-naphthyl]1-ethanone (compound A) and 11 mg (56%) of 1-[6-(ethyl-[2-(8-3-[2-(4-fluorophenyl)-1,3-dioxolan-2-yl]-propyl -1-oxo-4-phenyl-2,4,8-triazaspiro[4.5]dec-2-yl)-ethyl]amino-2-naphthyl)-1-ethanone (compound B).

Compound A—HRMS calcd. for $C_{41}H_{47}FN_4O_4$: 678.3581. Found: 678.3605. $^1$H NMR: δ1.45–2.24 (m, 11H, spiperone $CH_2$, $CH_2\underline{CH_3}$), 2.35–2.84 (m, 6H, spiperone), 2.65 (s, 3H. $OCH_3$), 3.59 (q, 2H, $N\underline{CH_2}CH_3$), 2.35–2.84 (M, 6H, spiperone), 2.65 (s, 3H, $OCH_3$), 3.59 (q, 2H, N $\underline{CH_2}CH_3$), 3.76 in 4.05 (m, 4H, $OCH_2CH_2O$), 3.85 (t, 2H, N $\underline{CH_2}CH_2O$), 4.52 (t, 2H, $O\underline{CH_2}CH_2N$), 4.99 (s, 2H, $NCH_2N$), 6.76–6.83 9m, 3H, phenyl, fluorophenyl), 6.93 (d, 1H, 5-H), 6.95–7.04 (M, 2H, phenyl, fluorophenyl), 7.19 (dd, 1H, 7-H), 7.21–7.26 (m, 2H, phenyl, fluorophenyl), 7.39–7.45 (m, 2H, phenyl, fluoropheynl), 7.61 (d, 1H, 4-H), 7.78 (d, 1H, 8-H), 7.93 (dd, 1H, 3-H), 8.30 (d, 1H, 1-H). $J_{1,3}$=1.5 Hz, $J_{5,7}$=2.4 Hz, $J_{3,4}$=9.5 Hz, $J_{7,8}$=9.2 Hz, $J_{(CH2CH3)}$=7.1 Hz, $J_{(NCH2CH2O)}$=6.3 Hz.

Compound B—HRMS calcd. for $C_{41}H_{47}FN_4O_4$: 678.3581. Found: 678.3603. $^1$H NMR: δ1.20–1.94 (m, 17H, spiperone $CH_2$, $CH_2\underline{CH_3}$), 2.66 (s, 3H, $COCH_3$), 3.56 (q, 2H, $N\underline{CH_2}CH_3$), 3.66 and 4.02 (m, 4H, $OCH_2CH_2O$), 3.71–3.81 (m, 4H, $NCH_2CH_2N$), 4.68 (s, 2H, $NCH_2N$), 6.82–6.90 (m, 2H, phenyl, fluorophenyl), 6.94 (d, 1H, 5-H), 6.98–7.04 (m, 2H, phenyl, fluorophenyl), 7.18 (dd, 1H, H-7), 7.21–7.26 (m, 3H, phenyl, fluorophenyl), 7.39–7.45 (m, 2H, phenyl, fluorophenyl), 7.60 (d, 1H, 4-H), 7.78 (d, 1H, 8-H), 7.93 (dd, 1H, 3-H), 8.29 (d, 1H, 1-H). $J_{1,3}$=1.6 Hz, $J_{3,4}$9.8 Hz. $J_{5,7}$=2.4 Hz, $J_{7,8}$=10.4 Hz, $J(CH2CH3)$=7.1 Hz.

A solution of 1-[6-(ethyl-[2-(8-3-[2-(4-fluorophenyl)-1,3-dioxolan-2-yl]-propyl-1-oxo-4-phenyl-2,4,8-tri-azaspiro [4.5]dec-2-yl)-ethyl]amino-2-naphthyl)-1-ethanone (13 mg, 0.018 mmol) and malononitrile (6 mg, 0.09 mmol) in pyridine (3 mL) was heated at 85° C. under argon for 24 hours. After pyridine was removed in vacuo at room temperature, the residue was distributed between brine and dichloromethane, and the organic layer was dried and evaporated. The product, 2-[1-(6-ethyl-[2-(8-3-[2-(4-fluorophenyl)-1,3-dioxolan-2-yl]-propyl-1-oxo-4-phenyl-2, 4,8-triazoaspiro[4.5]dec-2-yl)-ethyl]-amino-2-naphthyl)-ethylidene]-malononitrile was isolated by radial chromatography (1 mm silica, 2.5% methanol in dichloromethane; 13.5 mg, 97%).

HRMS calcd. for $C_{44}H_{48}FN_6O_3$ (M+H): 727.37719. Found: 727.3772. $^1$H NMR: δ1.25–1.93 (m, 17H, spiperone $CH_2$, $CH_2\underline{CH_3}$), 2.70 (s, 3H, C═C—$CH_3$), 3.57 (q, 2H, $NCH_2CH_3$), 3.64 and 4.03 (m, 4H, $OCH_2CH_2O$), 3.71–3.78 (m, 4H, $NCH_2CH_2N$), 4.68 (s, 2H, $NCH_2N$), 6.83–6.88 (m, 2H, phenyl, fluorophenyl), 6.94 (d, 1H, 5-H), 6.96–7.04 (m, 2H, phenyl, fluorophenyl), 7.18 (dd, 1H, H- 7), 7.21–7.25 (m, 3H, phenyl, fluorophenyl), 7.39–7.45 (m, 2H, phenyl, fluorophenyl), 7.56 (dd, 1H, 3-H), 7.63 (d, 1H, 4-H), 7.76 (dd, 1H, 9-H), 8.00 (d, 1H, 1-H). $J_{1,3}$=1.9 Hz, $J_{3,4}$=8.8 Hz, $J_{5,7}$=2.4 Hz, $J_{7,8}$=9.3 Hz, $J_{(CH2CH3)}$=7.1 Hz.

The ketal protective group was removed by stirring 2-[1-(6-ethyl-[2-(8-3-[2-(4-fluorophenyl)-1,3 -dioxolan-2-yl]-propyl-1-oxo-4-phenyl-2,4,8-triazaspiro[4.5]dec-2-yl)-ethyl]-amino-2-naphthyl)-ethylidene]-malononitrile (13.5 mg, 0.0186 mmol) in methanol (1 mL) with one drop of concentrated hydrochloric acid for 3 hours at room temperature. The reaction mixture was diluted with dichloromethane and washed with a saturated solution of sodium bicarbonate. After evaporation in vacuo, the residue was purified by radial chromatography (1 mm silica, 2% methanol in dichloromethane) to give 10 mg (79%) of 2-(1-6[ethyl-(2-8-[4-(4-fluorophenyl)-4-oxobutyl]-1oxo-4-phenyl-2,4,8-triazaspiro[4.5]dec-2-ylethyl)-amino]-2-naphthylethylidene)-malononitrile. FAB MS calcd for $C_{42}H_{44}FN_6O_2$ (M+H): 683.35. Found 683. $^1$H NMR: δ1.21–3.02 (m, 17H, spiperone $CH_2CH_3$), 2.71 (s, 3H, C═C—$CH_3$), 3.56 (q, 2H, $N\underline{CH_2}CH_3$), 3.69 (m, 4H, $NCH_2CH_2N$), 4.67 (s, 2H, $NCH_2N$), 6.79–7.23 (m, 7H, phenyl, fluorophenyl), 6.95 (d, 1H, 5-H), 5.19 (dd, 1H, 7-H), 7.56 (dd, 1H, 3-H), 7.65 (d, 1H, 4-H), 7.76 (d, 1H, 8-H), 7.97–8.04 (m, 3H, fluorophenyl, 1-H). $J_{1,3}$=1.9 Hz, $J_{3,4}$=8.8 Hz, $J_{5,7}$=2.5 Hz, $J_{7,8}$=9.1 Hz, $J_{(CH2CH3)}$=7.1 Hz.

Example 1(c) —2-(1-6-[4-(8-[4-(4-Fluorophenyl)-4-oxobutyl]-1-oxo-4-phenyl-2,4,8-triazaspiro[4.5]dec-2-ylmethyl)-piperidino]-2-naphthylethylidene)-malononitrile

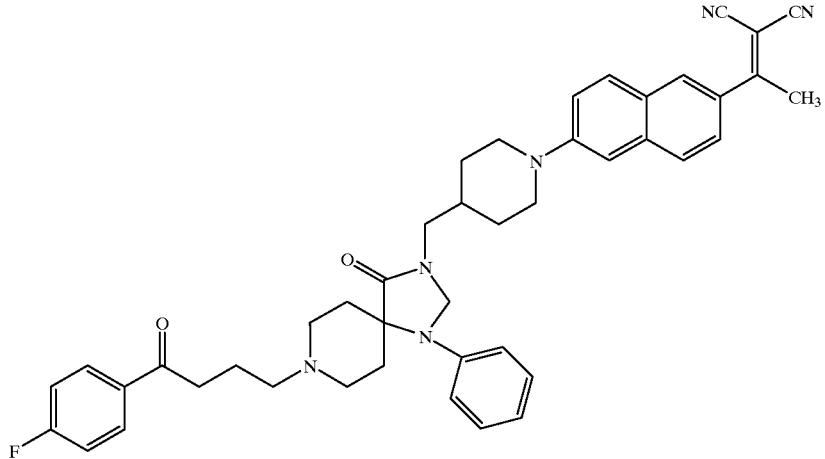

A mixture of 1-(6-hydroxy-2-naphthyl)-1-ethanone (653 mg, 3.5 mmol) (prepared as described in Example 1(b)), sodium hydrogensulfate(IV) (1.6 g, 15.5 mmol), 4-piperidylmethanol (2 g, 17.6 mmol) (prepared as described in Bradbury et al., J. Med. Chem. 34:1073 (1991), the disclosure of which is incorporated herein by reference), and water (6 mL) was heated in a steel bomb at 135–142° C. for 16 days. After cooling, the reaction mixture was extracted with ethyl acetate. Some product still remained in the residue, so it was further extracted with 5% methanol in dichloromethane. Organic extracts were combined, dried and evaporated. The residue was chromatographed by radial chromatography (2 mm silica, 2% methanol in dichloromethane) to yield 139 mg (14%) of 1-6-[(4-hydroxymethyl)-piperidino]-2-naphthyl-1-ethanone. After recrystallization from ethyl acetate the compound melted at 180–182° C. $^1$H NMR: $\delta$1.44 (dddd, 2H, 3'a-H, 5'a-H), 1.76 (m, 1H, 4'a-H), 1.91 (bd, 2H, 3'e-H, 5'c-H), 2.68 (s, 3H, COCH$_3$), 2.89 (ddd, 2H, 2'a-H, 6'a-H), 3.58 (d, 2H, OCH$_2$), 3.94 (bd, 2H, 2'e-H, 6'e-H), 7.10 (d, 1H, 5-H), 7.32 (dd, 1H, 7-H), 7.66 (d, 1H, 4-H), 7.80 (d, 1H, 8-H), 7.94 (dd, 1H, 3-H), 8.32 (d, 1H, 1-H) $J_{3'a,3'e}=J_{5'a,5'e}=12.5$ Hz, $J_{2'a,3'a}=J_{6'a,5'a}=12.5$ Hz, $J_{3'a,4'a}=J_{5'a,4'a}=12.5$ Hz, $J_{2'e,3'a}=J_{6'e,5'a}=4.0$ Hz, $J_{2'a,2'c}=J_{6'a,6'e}=12.5$ Hz, $J_{2'a,3'e}=J_{6'a,5e}=2.6$ Hz $J_{4a,OCH2}=6.4$ Hz, $J_{1,3}=1.9$ Hz, $J_{3,4}8.9$ Hz $J_{5,7}=2.3$ Hz, $J_{7,8}=9.0$ Hz.

A solution of 1-6-[(4-hydroxymethyl)-piperidino]-2-naphthyl-1-ethanone (59 mg, 0.2 mmol) in pyridine (3 ml,) was cooled to −15° C., and p-toluenesulfonic anhydride (205 mg, 0.6 mmol) was added with stirring under argon. The reaction mixture was allowed to slowly warm up to the room temperature during 1 hour. It was cooled again and distributed between brine and ether. The organic layer was washed with brine, dried and evaporated to leave 83 mg (91%) of raw 1-(6-acetyl-2-naphthyl)-4-[(4-methylphenyl)-sulfonyloxy]-methylpiperidine.

To a solution of sodium hydroxide (1 g) and tetra-n-butylammonium hydrogen-sulfate(VI) (50 mg, 0.15 mmol) in water (2 mL), spiperone ketal (100 mg, 0.2 mmol) was added and vigorously stirred. After 10 minutes, a solution of 1-(6-acetyl-2-naphthyl)-4-[(4-methylphenyl)-sulfonyloxy]-methylpiperidine (98 mg, 0.2 mmol) in toluene (10 mL) was added, and the reaction mixture was stirred at room temperature for 11 days. The reaction mixture was distributed between brine and dichloromethane, and the organic layer was dried and evaporated to leave 190 mg of an oily residue. Radial chromatography (1 mm silica, dichloromethane followed by 2% methanol in dichloromethane) yielded 27 mg (17%) of 1-[6-(4-[(8-3-[2-(4-fluorophenyl)-1,3-dioxolan-2-yl]-propyl-4-phenyl-2,4,8-triazaspiro[4.5]dec-1-en-1-yl)-oxyl-methylpiperidino)-2-naphthyl]-1-ethanone (compound 3) and 92 mg (58%) of 1-(6-4-[(8-3-[2-(4-fluorophenyl)-1,3-dioxolan-2y-1]-propyl-1-oxo-4-phenyl-2,4,8-triazaspiro[4.5]dec-2-yl)-methyl]-piperidino-2-naphthyl)-1-ethanone (compound 4).

Compound 3: HRMS calcd. for $C_{43}H_{49}FN_4O_4$: 704.3738. Found: 704.3760. $^1$H NMR $\delta$1.46–1.90 (m, 10H, 3'a-H, 5'a-H, 3'e-H, 5'e-H, spiperone), 1.88 (m, 1H, 4'a-H), 2.15 and 2.38 (b, 4H, spiperone), 2.67 (s, 3H, COCH$_3$), 2.80 (m, 4H, spiperone), 2.95 (m, 2H, 2'a-H, 6'a-H), 3.75 (m, 2H, OCH$_2$CH$_2$O), 3.87 (m, 2H, 2'e-H, 6'e-H), 3.92 (m, 2H, OCH$_2$CH$_2$O), 4.19 (d, 2H, OCH$_2$), 4.97 (s, 2H, NCH$_2$N), 6.7–6.9 (m, 3H, Ph), 7.01 (m, 2H, Ph), 7.11 (d, 1H, 5-H), 7.23 (m, 211, Ph), 7.32 (dd, 1H, 7-H), 7.41 (m, 2H, Ph), 7.66 (d, 1H, 4-H), 7.81 (d, 1H, 8-H), 7.95 (dd, 1H, 3H), 8.32 (d 1H, 1-H), $J_{2'a,2'e}=J_{6'a,6'e}=12.4$ Hz, $J_{2'a,3'e}=J_{6'a,5'e}=2.6$ Hz, $J_{4'a,OCH2}=6.1$ Hz, $J_{1,3}=0.1$ Hz, $J_{3,4}=8.8$ Hz, $J_{5,7}=2.1$ Hz, $J_{7,8}=9.1$ Hz.

Compound 4: HRMS calcd. for $C_{43}H_{49}FN_4O_4$: 704.3738. Found: 704.3710. $^1$H NMR $\delta$1.50 (dddcl, 2H, 3'a-H, 5'a-H), 1.55–1.70 (m, 4H, spiperone), 1.84 (bd, 2H, 3'e-H, 5'e-H), 1.92 (m, 2H, spiperone), 1.98 (m, 1H, 4'a-H), 2.42 (m, 2H, spiperone), 2.67 (s, 3H, COCH$_1$), 2.69 (m, 2H, spiperone), 2.83 (m, 4H, spiperone), 2.88 (m, 2H, 2'a-H, 6'a-H), 3.35 (d, 2H, 4'-CH$_2$N), 3.75 (m, 2H, OCH$_2$CH$_2$O), 3.92 (bd, 2H, 2'e-H, 6'e-H), 4.02 (m, 2H, OCH$_2$CH$_2$O), 4.71 (s, 2H, NCH$_2$N), 6.88 (m, 1H, Ph), 6.91 (m, 2H, Ph), 7.01 (m, 2H, Ph), 7.08 (bs, 1H, 5-H), 7.27 (m, 3H, 7-H, Ph). 7.43 (m, 2H, Ph), 7.65 (d, 1H, 4-H), 7.79 (d, 1H, 8-H), 7.94 (dd, 1H, 3-H), 8.32 (bs, 1H, 1-H), $J_{3'a,3'e}=J_{5'a,5'e}=12.4$ Hz, $J_{2'a,3'a}=12.5$ Hz, $J_{2'a,2'e}=J_{6'a,6'e}=12.8$ Hz, $J_{2'a,3'e}=J_{6'a,5'e}=2.4$ Hz, $J_{4'a,4'}$-CH$_2$N= 7.3 Hz, $J_{1,3}=1.9$ Hz, $J_{3,4}=8.8$ Hz, $J_{5,7}=2.1$ Hz, $J_{7,8}=9.2$ Hz.

Using the procedure described in Example 1(b) for the synthesis of 2-[1-(6-ethyl-[2-(8-3-[2-(4-fluorophenyl)-1,3-dioxolan-2-yl]-propyl-1-oxo-4-phenyl-2,4,8-triazoaspiro [4.5]dec-2-yl)-ethyl]-amino-2-naphthyl)-ethylidene]-malonitrile, 1-(6-4-[(8-3-[2-(4-fluorophenyl)-1,3-dioxolan-2y-1]-propyl-1-oxo-4-phenyl-2,4,8-triazaspiro[4.5]dec-2- yl)-methyl]-piperidino-2-naphthyl)-1-ethanone was transformed into 2-[1-(6-4-[(8-3-[2-(4-fluorophenyl)-1,3-dioxolan-2y-1]-propyl-1-oxo-4-phenyl-2,4,8-triazaspiro[4.5]dec-2-yl)-methyl]-piperidino-2-naphthyl)-ethylidene] malonitrile. It was purified by radial chromatography on a 1 mm silica plate using 2% MeOH in $CH_2Cl_2$ as the solvent. FAB HRMS calcd. for $C_{46}H_{50}FN_6O_3$ (M+H): 753.3928. Found: 753.3940. $^1$H NMR δ1.60–2.1 (m, 11H, spiperone, 3'a-H, 3'e-H, 4'a-H, 5'a-H, 5'e-H, 2.40 (m, 2H, spiperone), 2.71 (s, 3H, C=CCH$_3$). 2.60–2.80 (m, 6H, spiperone), 2.91 (m, 2H, 2'a-H, 6'a-H), 3.37 (d, 2H, 4'-CH2N), 3.75 (m, 2H, OCH$_2$CH$_2$O), 3.94 (bd, 2H, 2'e-H, 6'e-H), 4.02 (m, 2H, OCH$_2$CH$_2$O), 4.72 (s, 2H, NCH$_2$N), 6.85–6.95 (m, 3H, Ph), 7.01 (m, 2H, fluorophenyl), 7.07 (d, 1H, 5-H), 7.31 (m, 3H, 7-H, Ph), 7.41 (m, 2H, fluorophenyl), 7.56 (dd, 1H, 3-H), 7.69 (d, 1H, 4-H), 7.77 (d, 1H, 8-H), 8.01 (d, 1H, 1-H), $J_{2'a,3'a}=J_{5'a,6'a}=12.8$ Hz, $J_{2'a,2'e}=J_{6'a,6'e}=12.8$ Hz, $J_{4'a,4'-CH2N}=7.6$ Hz, $J_{1,3}32$ 1.8 Hz, $J_{3,4}32$ 8.6 Hz, $J_{5,7}=2.2$ Hz, $J_{7,8}=9.4$ Hz, $J_{2'a,3'e}=J_{5'e,6'a}=1.8$ Hz, $J_{H,F}=8.7$ and 6.2 Hz.

The ketal protective group was removed, as described in Example 1(b), to give 2-(1-6-[4-(8-[4-(4-fluorophenyl)-4-oxobutyl]-1-oxo-4-phenyl-2,4,8-triazaspiro[4.5]-dec-2-ylmethyl)-piperidino]-2-naphthylethylidene)-malononitrile in a quantitative yield. FAB HRMS calcd. for $C_{44}H_{46}FN_6O_2$ (M+H): 709.3666. Found: 709.3689. $^1$H NMR δ1.60–2.1 (m, 11H, spiperone, 3'a-H, 3'e-H, 4'a-H, 5'a-H, 5'e-H), 2.5–2.71 (m, 4H, spiperone), 2.73 (s, 3H, C=C—CH$_3$), 2.8–3.1 (m, 6H, spiperone, 2'a-H, 6'a-H), 3.38 (d, 2H, 4'-CH$_2$N), 3.96 (bd, 2H, 2'e-H, 6'e-H), 4.74 (s, 2H, NCH$_2$N), 6.91 (m, 3H, phenyl), 7.1 (d, 1H, 5-H), 7.15 (m, 2H, fluorophenyl), 7.24–7.30 (m, 2H, Ph), 7.34 (dd, 1H, 7-H), 7.58 (dd, 1H, 3-H) 7.72 (d, 1H, 4-H), 7.79 (d, 1H, 8-H), 8.01–8.08 (m, 3H, fluorophenyl, 1-H). $J_{1,3}=2.0$ Hz, $J_{3,4}= 8.6$ Hz, $J_{5,7}=2.4$ Hz, $J_{7,8}=9.2$ Hz, $J_{4'a,4'-CH2N}=7.4$ Hz,, $J_{2'a,2'e}=J_{6'a,6'e}=13.0$ Hz, $J_{2'a,3'a}=J_{5'a,6'a}=12.5$ Hz, $J_{2'a,3'e}=J_{5'e,6'a}=1.9$ Hz, $J_{H,F}=8.7$ and 6.2 Hz.

Example 1(d)—Preparation of tert-Butyl-4-(6-acetyl-2-nahthyl)-1-piperazinecarboxylate

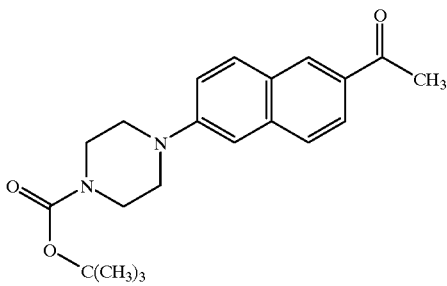

Anhydrous piperazine (7 g, 81.3 mmol; dried in a vacuum desiccator over KOH-drierite mixture for 3 days) was dissolved in a mixture of dry, freshly distilled toluene and hexamethyl phosphoric amide (HMPA), 25 mL each. To the solution was added 556 mg (80.1 mmol) of lithium rod, cut in small pieces under argon atmosphere, and the mixture was stirred under argon for 24 hours, during which time all lithium has dissolved. Vacuum-dried 1-(6-methoxy-2-naphthyl)-1-ethanone (prepared as described in Arsenijevic et al., Org. Synth. Coll. 1988 6:34–36, the disclosure of which is incorporated herein by reference) (3.5 g, 17.5 mmol) was added and stirring was continued for additional 65 hours. After quenching with 300 mL of water, extraction with dichloromethane (3×300 ml,), drying with anhydrous magnesium sulfate, and evaporation, a mixture of white and yellow solids was obtained. Extraction with 300 mL of hot methanol gave raw product, 1-(6-piperazino-2-naphthyl)-1-ethanone, which was purified by column chromatography (70–230 mesh silica, 25×120 mm, 5% methanol in dichloromethane). The yield was 1.54 g (35%). After recrystallization from ethyl acetate, the sample melted at 170.5–172° C.

1-(6-piperazino-2-naphthyl)-1-ethanone was also prepared by heating 1-(6-hydroxy-2-naphthyl)-1-ethanone (prepared as described in Example 1(b)) (441 mg, 2.36 mmol) at 140–150° C. with 6 g piperazine hydrate (30.9 mmol) and 244 mg (2.35 mmol) NaHSO$_3$ for 24 hours. Additional sodium bisulfite (2 g, 19.2 mmol) was added. After an additional 24 hours, more bisulfite (1 g) was added, and heating was continued (total reaction time 72 hours). After cooling, the mixture was extracted with 2×50 mL methanol. The residue after evaporation of methanol was suspended in 50 mL water and extracted with ethyl acetate (5×80 mL). Combined extracts were dried (magnesium sulfate) and evaporated to give 430 mg of yellow solid. Radial chromatography (4 mm silica, methanol) gave 83 mg (19%) of starting naphthol and 276 mg (46%; 56%, based on unrecovered starting material) of 1-(6-piperazino-2-naphthyl)-1-ethanone. The 1-(6-piperazino-2-naphthyl)-1-ethanone was in all respects identical with the compound obtained using the alternative method described above. Anal. calculated for $C_{16}H_{18}N_2O$: C, 75.56; H, 7.13; N, 11.01. Found: C, 75.82; H, 7.27; N, 10.92. $^1$H NMR: δ2.68 (s, 3H, CH$_3$), 3.09 and 3.35 (t, J=4.95 Hz, 8H, piperazine), 7.10 (d, 1H, 5-H), 7.31 (dd, 1H, 7-H), 7.69 (d, 1H, 4-H), 7.83 (d, 1H, 8-H), 7.95 (d, 1H, 8.34 (s, 1H, 1-H); $J_{5,7}=2$ Hz, $J_{7,8}=8.4$ Hz, $J_{1,3}=2$ Hz, $J_{3,4}=8.4$ Hz.

1-(6-piperazino-2-naphthyl)-1-ethanone (254 mg, 1 mmol) was added to a stirred mixture of 1 g NaOH, 100 mg tetia-n-butylammonium hydrogensulfate, 2 mL water and 6 mL toluene, followed by a solution of 230 mg (1.05 mmol) of di-tert-butyl dicarbonate. The course of the reaction was followed by TLC (silica, 5% methanol in dichloromethane). Every 10 minutes an additional amount of the dicarbonate was added until all starting material had reacted. A total of approximately 1.5 equivalents were used. A mixture of water and dichloromethane (60 mL each) was added, and, after thorough shaking, the layers were separated. The aqueous layer was extracted with an additional 30 mL of dichloromethane. The combined organic extracts were dried with anhydrous magnesium sulfate. During this procedure, the color of the solution turned from pink to light yellow. Evaporation in vacuo gave 295 mg (83%) of tert-butyl-4-(6-acetyl-2-naphthyl)-1-piperazinecarboxylate, which, on recrystallization from dichloromethane-petroleum ether mixture, melted at 153–154° C. Anal. Calculated for $C_{21}H_{26}N_2O_3$: C, 71.16; H, 7.39; N, 7.90. Found: C, 71.27; H, 7.60; N, 7.86. $^1$H NMR: δ1.50 (s, 9H, —C(CH$_3$)$_3$), 2.68 (s, 3H, CH$_3$), 3.33 and 3.64 (t, J=4.9 Hz, 8H, piperazine), 7.10 (d, 1H, 5-H), 7.31 (dd, 1H, 7H), 7.70 (d, 1H, 4-H), 7.85 (d, 1H, 8-H), 7.97 (d, 1H, 3-H), 8.35 (d, 1H, 1-H); $J_{5,7}=2$ Hz, $J_{7,8}=9$ Hz, $J_{3,4}=8.7$ Hz.

Example 1(e)—Preparation of 2-[1-(6-piperazino-2-naphthyl)ethylidene]malononitrile

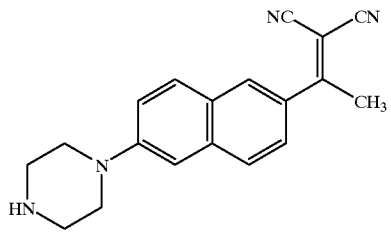

tert-Butyl 4-(6-acetyl-2-naphthyl)-1-piperazinecarboxylate (177 mg, 0.5 mmol), prepared as described in Example 1(d), was heated with 40 mg (0.6 mmol) of malononitrile in 4 mL pyridine at 105–1 10C. After 5.5 hours, an additional 24 mg of malononitrile was added, and heating was continued for a total of 12 hours and 40 minutes. The mixture was cooled and evaporated in vacuo. Polar components of the mixture were removed by column chromatography (70–230 mesh silica, φ20×120 mm, chloroform), and the product, tert-butyl-4-[6-(2,2-dicyano-1-methylvinyl)-2-naphthyl]-1-piperazinecarboxylate, was finally purified by radial chromatography (silica, 2 mm, chloroform). 155 mg (77%) of tert-butyl-4-[6-(2,2-dicyano-1-methylvinyl)-2-naphthyl]-1-piperazinecarboxylate were obtained, which, after recrystallization from dichloromethane—petroleum ether mixture, melted at 169–171° C. Anal. Calculated for $C_{24}H_{26}N_4O_2$: C, 71.62; H, 6.51; N, 13.92. Found: C, 71.62; H, 6.66; N, 13.87. $^1$H NMR: δ1.50 (s, 9H, —C(CH$_3$)$_3$), 2.72 (s, 3H, CH$_3$), 3.34 and 3.64 (t, J=5.1 Hz, 8H, piperazine), 7.09 (d, 1H, 5-H), 7.33 (dd, 1H, 7-H), 7.58 (dd, 1H, 3-H), 7.74 (d, 1H, 4-H), 7.81 (d, 1H, 8-H), 8.02 (d, 1H, 1-H); $J_{5,7}$=2 Hz, $J_{7,8}$=9.1 Hz, $J_{1,3}$=2 Hz, $J_{3,4}$=9.1 Hz.

When tert-butyl-4-[6-(2,2-dicyano-1-methylvinyl)-2-naphthyl]-1-piperazinecarboxylate was treated with TFA (trifluoroacetic acid) at room temperature, TLC showed that the reaction was over in 5 minutes and gave a single product, 2-[1-(6-piperazino-2-naphthyl)ethylidene]malononitrile. The TFA was removed in vacuo at room temperature. $^1$H NMR: δ2.72 (s, 3H, CH$_3$), 3.50 and 3.63 (broad, 8H, piperazine), 7.18 (broad s, 1H, 5-H), 7.29 (d, 1H, 7-H), 7.59 (d, 1H, 3-H), 7.79 (d, 1H, 4-H), 7.87 (d, 1H, 8-H), 8.04 (s, 1H, 1-H), 9.0 (broad, 1.5H, NH and acid); $J_{7,8}$=8.8 Hz, $J_{3,4}$=8.4 Hz. $^{19}$F NMR: δ–76.2 (CF$_3$COO).

NMR of the residue revealed that the tert-butyloxycarbonyl group has been removed and that there was some TFA left ($^{19}$F NMR). Dichloromethane (10 mL) was added and the solution was washed with saturated NaHCO$_3$ solution, dried, and evaporated in vacuo. A light yellow oil was obtained, which, on standing at room temperature, turned dark red. TLC showed that the change in color is due to decomposition of 2-[1-(6-piperazino-2-naphthyl)ethylidene]malononitrile into several products, the most intense spot being low-$R_f$ red-orange. Selected $^1$H NMR signals after neutralization: δ2.72 (s, 3H, CH$_3$), 3.09 and 3.35 (t, J=5 Hz, 8H, piperazine), 7.08 (s, 1H, 5-H, 8.02 (s, 1H, 1-H).

Example 1(f)—Preparation of 2-(1.1-dicyanopropen-2-yl)-6-(2-[$^{18}$-F]-fluoroethyl)-methylamino)-naphthalene ([F-18]FDDNP)

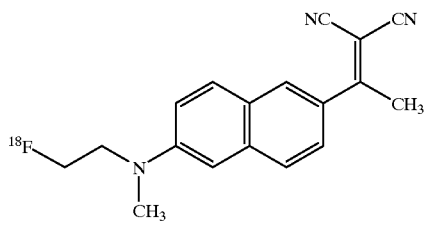

A mixture of 4.15 g (55.5 mmol) NaHSO$_3$, 8 mL of water, 0.78 g (4.19 mmol) of 1-(6-hydroxy-2-naphthyl)-1-ethanone (prepared as described in Example 1(b)), and 8 mL of 2-methylaminoethanol was heated and stirred in a steel bomb at 140° C. for 28 hours. After cooling, the mixture was distributed between ethyl acetate and water (500 mL and 200 mL, respectively). The organic layer was dried and evaporated to leave raw 1-(6-(2-hydroxyethyl-methylamino)-2-naphthyl)-1-ethanone (0.749 g, 73%) of which was further purified by radial chromatography (4 mm SiO$_3$, CH$_2$Cl$_2$).

To a solution of 201 mg (0.83 mmol) of 1-(6-2-hydroxyethyl-methylamino-2-naphthyl)-1-ethanone in pyridine (6 mL), malononitrile (236 mg, 3.6 mmol) was added and the mixture was heated at 95° C. for 24 hours. The solvent was removed in vacuo, and the residue was chromatographed by radial chromatography (4 mm SiO$_2$ 1% MeOH/CH$_2$Cl$_2$) to give 150 mg (73%) of 2-(1,1-dicyanopropen-2-yl)-6-2-hydroxyethyl)-methyl-amino)-naphthalene.

To the solution of 2-(1,1-dicyanopropen-2-yl)-6-(2-hydroxyethyl)-methylamino)-naphthalene (120 mg, 0.41 mmol) in pyridine (5 mL), p-toluensulfonic anhydride was added (441 mg, 1.35 mmol). After stirring at room temperature for 1 hour, pyridine was removed under vacuum, and the residue was chromatographed by radial chromatography (2 mm SiO$_2$, CH$_2$Cl$_2$) to give 183 mg (80%) of 2-(1,1-dicyanopropen-2-yl)-6-(2-tosyloxyethyl)-methylamino-naphthalene.

Radioactive $^{18}$F-fluoride 528.5 mCi from the cyclotron was transferred into a solution of 19 mg of Kryptofix 2.2.2 and 0.75 mg potassium carbonate in 50 μL of water and 300 μL of acetonitrile. Water was removed in a stream of nitrogen at 115° C. followed by codistillation with acetonitrile (3×200 μL). The tosylate (2-(1,1-dicyanopropen-2-yl)-6-(2-tosyloxyethyl)-methylamino)-naphthalene, 4 mg) in 1 mL of acetonitrile was added, and the mixture was heated at 85–86° C. for 20 minutes. After cooling, 1 mL of water was added, and the mixture was transferred onto a C-18 Sep-Pak Cartridge, washed with distilled water (3×4 mL) and eluted with CH$_2$Cl$_2$ (2×2.5 mL). Eluate was dried by passing through a column packed with sodium sulfate and loaded onto a HPLC column (Whatman Partisil Silica 10, 500×10 mm, mL/min CH$_2$Cl$_2$:hexane=7:3, UV detector @254 nm, radioactivity detector). Eluate was collected, appropriate fractions were combined, evaporated under vacuo to yield 50.7 mCi (17%, corrected for decay) of the titled product which was formulated for injection. The synthesis was complete in 50 minutes.

Example 2

Detection and labeling of β-amyloid plaques in vitro and in vivo, using brain tissue sections and rat brains, were conducted using the following procedures.

A 2.1 mg/mL DDNP stock solution was prepared, which was adjusted to 8 mM in 100% ethanol. A DDNP working solution was prepared by diluting the stock solution with distilled water in a ratio of 1:100–1000 (stock solution:distilled water).

β-amyloid 250 μM (1.25 mg/mL in distilled water) was aggregated at 37° C. for 48 hours. 5 μL were smeared on slides, air-dried and then rehydrated with distilled water. Alternatively, Aβ-positive brain tissue sections were rehydrated with distilled water. DDNP working solution was applied to each slide for 30 minutes at room temperature. The slides were washed three times for five minutes with distilled water. The slides were coverslipped with fluorescent protectant mounding media (Vectashield™, available Vector Labs., Burlingame, Calif.) and observed under a fluorescence microscope with a thioflavin S or FITC filter.

β-amyloid 250 μM (1.25 mg/mL in distilled water) was aggregated at 37° C. for 48 hours to produce fibrils confirmed by smears. Three rats were anesthetized. 3 μL of a solution of Aβ fibrils (1.25 μg/μL) were injected unilaterally into the cortex of each rat (Bregma 0, AP-4.1 mm, ML+2.0 mm, DV-3.1 mm). Then 3 μL of phosphate buffered saline (PBS) were injected into the contralateral side of each rat brain as a vehicle control. After injection, the needle remained for 5 minutes to prevent reflux, and then the cranial hole was sealed with bone wax. Eight days after β-amyloid injection into the rat brains, the rats were injected with 10 microliters of DDNP working solution (320 micromolar) prepared by diluting DDNP stock solution into 1.5% BSA (bovine serum albumin) in phosphate buffered saline, pH 7.2).

After one hour, the rats were cardiac perfused with PLP fixative (4% paraformaldehyde, 1% lysin in 0.05 M phosphate buffer, pH 7.4). Additional immersion fixation of rat brain was at 4° C. overnight with PLP fixative. The rat brains were washed with PBS, saturated in 10 and 20% sucrose, and snap frozen in chilled isopentane (−70° C.) with liquid nitrogen. The brains were cryostat sectioned at 10 μM around the needle-track and directly coverslipped with glycerol and fluorescence protectant (Vectashield™). The brain sections were observed with a fluorescence microscope.

FIGS. 1A to 1F depict amyloid plaques labeled in sections from brain of an AD patient and a transgenic mouse, demonstrating that DDNP is able to label amyloid plaques. FIGS. 2A to 2E depict labeled β-amyloid plaques, demonstrating that DDNP passes the blood brain barrier in rats.

It was found that DDNP readily labeled amyloid deposits in cryostat and paraffin sections of AD brain tissue with a level of sensitivity similar to thioflavin S. Use of DDNP has several advantages over thioflavin S. Namely, the use of DDNP requires no pretreatments and, unlike thioflavin S, works with minimal washing and without formalin or parafornaldehyde fixation or differentiation of tissue. Stock solution can be kept in the freezer for six months and still produce acceptable results at 1/100 to 1/1,000 dilutions, eliminating the need to make the stock up fresh, as is required for thioflavin S labeling.

Example 3

Labeling of human β-amyloid plaques and neurofibrillary tangles in vivo were conducted using the following procedures.

A patient was placed in a tomograph to obtain brain dynamic PET images. 8.0 mCi of 2-(1.1-dicyanopropen-2-yl)-6-(2-[$^{18}$F]-fluoroethyl)-methylamino)-naphthalene ([F18]FDDNP (specific activity: 5–12 Ci/micromol; mass:~1 nanomol), prepared as described in Example 1(f), were injected intravenously into the arm of the patient. Dynamic acquisition data of brain images were recorded simultaneously in forty-seven brain planes for two hours.

It was found that [F-18]FDDNP readily crosses the brain blood barrier and labels brain structures in a manner consistent with the presence of beta amyloid plaques and neurofibrillary tangles. The patient had previously had $^{18}$F-fluorodeoxyglucose (FDG)/positron emission tomography (PET) scans, as well as MRI scans to monitor brain atrophy. In areas where the maximum atrophy was observed in the MRI scans (low temporal and parietal lobes), maximum accumulation of the [F-18]FDDNP label was observed. In those areas, low glucose metabolism (as measured with FDG/PET scans) was also observed.

Example 4

Labeling and detection of human β-amyloid plaques and neurofibrillary tangles in vivo were conducted using the following procedures. Ten human subjects, seven Alzheimer's diseased patients (ages 71 to 80) and three control patients (ages 62 to 82) were studied. The patients were positioned supine in an EXACT HR+962 tomograph (Siemens-CTI, Knoxville, Tenn.) with the imaging plane parallel to the orbito-meatal line. Venous catheterization was performed, and then [F-18]FDDNP (5–10 mCi) in human serum albumin (25%) was administered as a bolus via the venous catheter. Sequential emission scans were obtained beginning immediately after [F-18]FDDNP administration using the following scan sequence: six 30 second scans, four 3 minute scans, five 10 minute scans, and three 20 minute scans. Rapid venous blood sampling was performed via the indwelling catheter in two subjects for input function determination and plasma metabolite analysis.

Figure 3A:
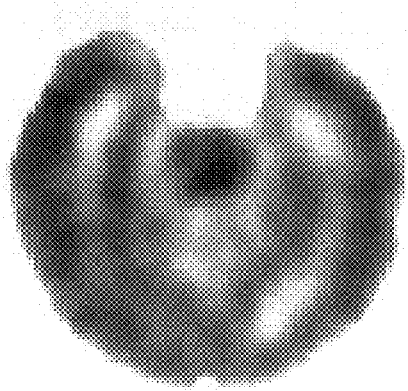
FIG. 3A is a PET-[F-18]FDDNP (2-(1.1-dicyanopropen-2-yl)-6-(2-[$^{18}$F]-fluoroethyl)-methylamino)-naphthalene) image of a brain cross-section through the hippocampus-amygdala-entorhinal/temporal cortex region of an Alzheimer's disease patient.
Figure 3B:
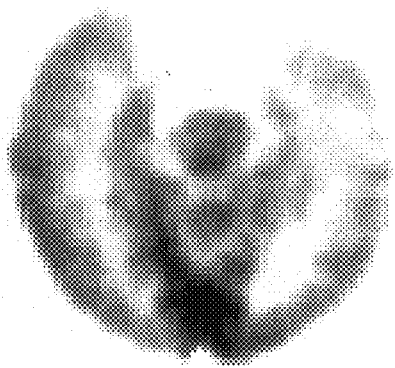
FIG. 3B is a PET-FDG (FDG is 2-[F-18]fluoro-2-deoxy-D-glucose) image of the brain cross-section of FIG. 3A.
Figure 3C:
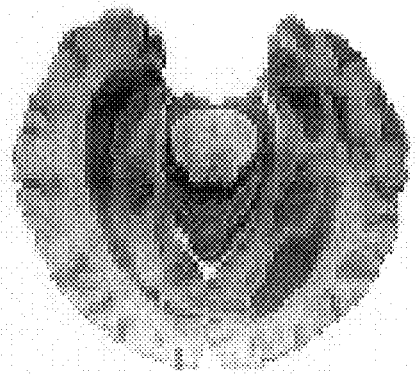
FIG. 3C is an MRI image (proton relaxation times) of the brain cross-section of FIG. 3A.

FIG. 3A provides a PET-[F-18]FDDNP (2-(1.1-dicyanopropen-2-yl)-6-(2-[$^{18}$F]-fluoroethyl)-methylamino)-naphthalene) image of a brain cross-section through the hippocampus-amygdala-entorhinal/temporal cortex region of an Alzheimer's disease patient. The image was reconstructed from scanning data obtained 30 to 60 minutes post [F-18]FDDNP injection. Co-registered PET-FDG (FDG is 2-[F-18]fluoro-2-deoxy-D-glucose) and MRI (proton relaxation times) images of the patient are also shown, in FIGS. 3B and 3C, respectively, to provide information about glucose metabolism and anatomical structures on the cross-section, respectively. The medial temporal region appears darker in the [F-18]FDDNP scan (slower clearance) and lighter in the FDG scan (reduced glucose metabolism).

Figure 4:
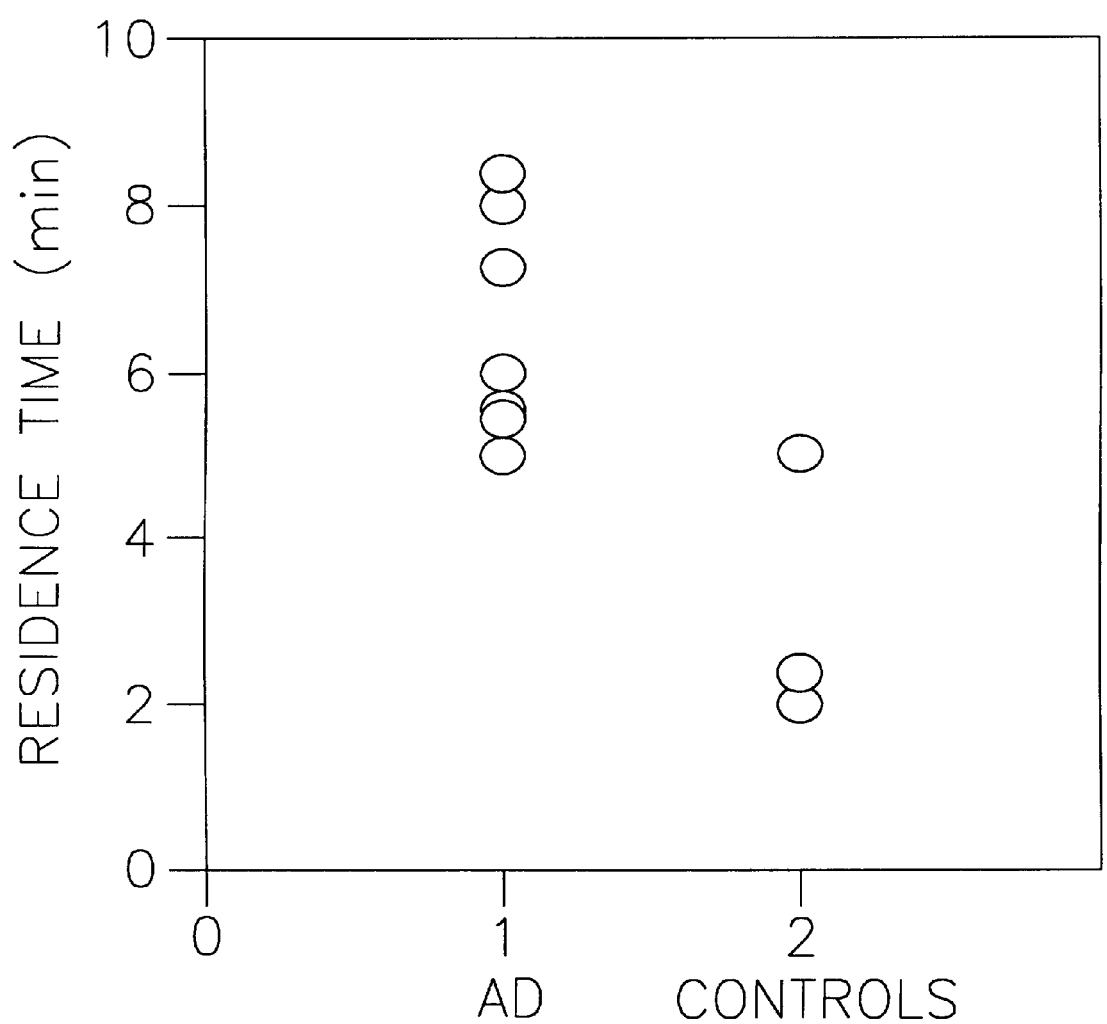
FIG. 4 is a graph showing the estimated residence times of [F-18]FDDNP in patients.

FIG. 4 demonstrates that estimated residence times of [F-18]FDDNP in Alzheimer's diseased patients are seen to be different from values in control patients. The residence time shown is in reference to that in the pons, an area known to have limited involvement in Alzheimer's disease pathology. The residence time was calculated from the clearance rates of the tracer in affected regions of interest (ROI) and in the pons as:

Residence time=[1/clearance rate for affected ROI]−[1/clearance rate for pons]

Separate ROIs were defined in entorhinal cortex, hippocampus, lateral temporal cortex and pons. The region with the slowest clearance rate was used as the affected ROI in the calculation of the residence time shown in FIG. 4.

It was found that after intravenous injection, [F-18] FDDNP crosses the blood brain barrier readily in proportion to blood flow. Accumulation of radioactivity was followed by the differential regional clearance of [F-18]FDDNP. A slower clearance was observed in brain areas reliably known to accumulate β-amyloid plaques and neurofibrillary tangles, specifically the hippocampus-amygdala-entorhinal complex, as well as temporal and parietal cortex in more advanced states of the disease. rCMRGl measured with PET in these subjects were also consistent with the expected β-amyloid plaque load and the possible presence of neurofibrillary tangles. In these patients, brain areas with low glucose metabolism were in general matched with high retention of [F-18]FDDNP. The hippocampus-amygdala-entorhinal cortex presented high retention of activity ([F-18]FDDNP) in most cases, even in patients with low severity of symptoms. A normal 82 year old volunteer presented deposition of activity in the hippocampus-amygdala-entorhinal complex in a PET study with [F-18]FDDNP, and low rCMRGl in the same areas, as measured with FDG, as shown in FIG. 4. These results are consistent with observations that elderly individuals without apparent signs of dementia may present neurofibrillary pathology in the second layer of neurons of the entorhinai cortex and plaques in the hippocampal formation. Increased severity of symptoms was always accompanied with increased retention of activity, and slow clearance from temporal, parietal or frontal cortex, in agreement with expected Aβ and neurofibrillary tangles deposition in these areas.

In vitro autoradiography using [F-18]FDDNP with brain specimens of Alzheimer diseased patients also demonstrated a distribution of activity consistent with the presence of β-amyloid plaques and neurofibrillary tangles. Binding was observed in hippocampus, temporal and parietal cortex matching results with immunostaining Aβ and tau antibodies. Since DDNP and its derivatives are fluorescent, an evaluation of the ability of [F-18]FDDNP to label β-amyloid plaques and neurofibrillary tangles in vitro was also performed with the same brain specimens. In all Alzheimer's disease brain specimens, excellent visualization of neurofibrillary tangles, amyloid peptides, and diffuse amyloid was produced with both DDNP and [F-18]FDDNP, matching results with thioflavin S (24) obtained with the same samples.

Figure 5:
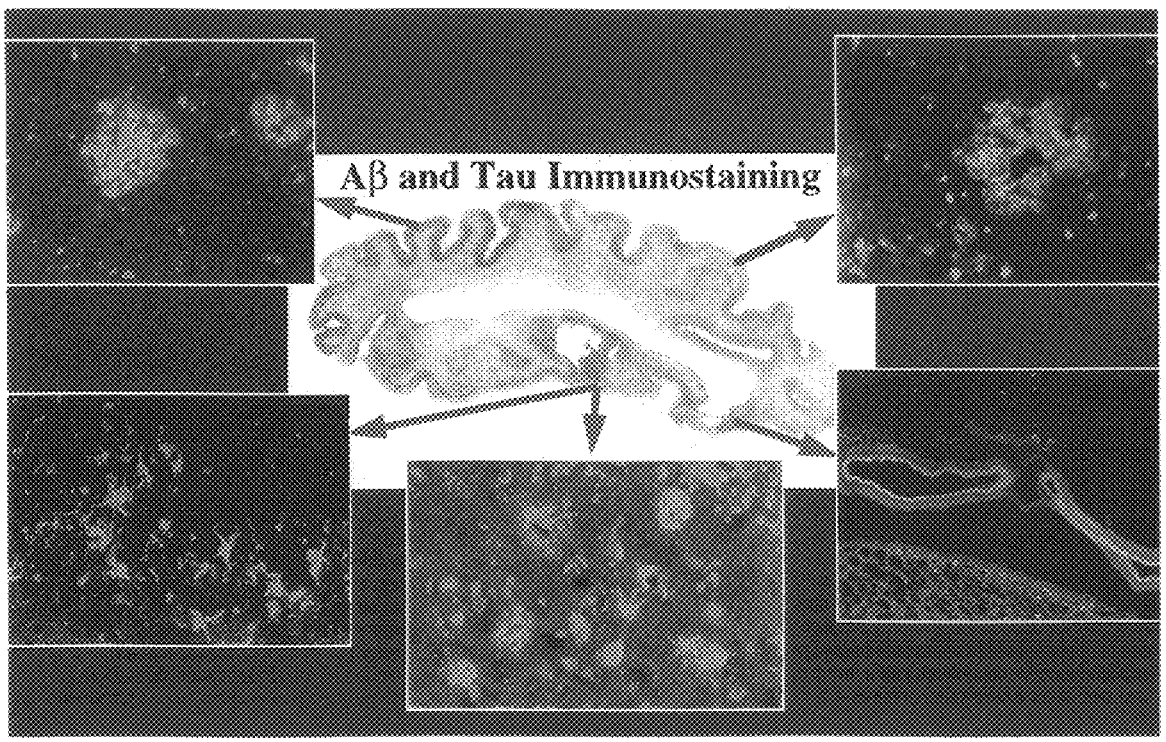
FIG. 5 shows an image (central image) obtained by immunostaining a forty five micrometer cryostate temporal cortex section of an Alzheimer's disease patient incubated with AT8 (anti-phosphotau) and 10G4 (anti-AB1-15) at 1:800. Insets are adjacent sections of the same Alzheimer's disease brain specimen stained with FDDNP showing, beginning in the upper left corner and moving clockwise, (1) neuritic plaques, (2) diffuse plaque, (3) vascular amyloid, (4) dense plaques and tangles, and (5) dense tangles.

In FIG. 5, the central image was obtained by immunostaining a forty five micrometer cryostate temporal cortex section of an Alzheimer's disease patient incubated with AT8 (anti-phosphotau) and 10G4 (anti-AB1-15) at 1:800. Insets are adjacent sections of the same Alzheimer's disease brain specimen stained with FDDNP. Images were generated using fluorescent scanning microscopy. Green arrows indicate approximate origin of inset with reference to central immunostaining section. Beginning in upper left corner and moving clockwise, the insets show (1) neuritic plaques, (2) diffuse plaque, (3) vascular amyloid, (4) dense plaques and tangles, and (5) dense tangles.

This invention in its broader aspect is not limited to the specific details shown and described herein. Departures from such details may be made without departing from the principles of the invention and without sacrificing its chief advantages.

We claim:
1. A method for labeling structures selected from the group consisting of β-amyloid plaques and neurofibrillary tangles in vivo, comprising:
contacting brain tissue with a compound of formula (I):

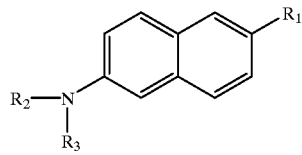

wherein:
R$_1$ is selected from the group consisting of —C(O)-alkyl, —C(O)-alkylenyl-R$_4$, —C(O)O-alkyl, —C(O)O-alkylenyl-R$_4$, —C=C(CN)$_2$-alkyl, —C=C(CN)$_2$-alkylenyl-R$_4$,

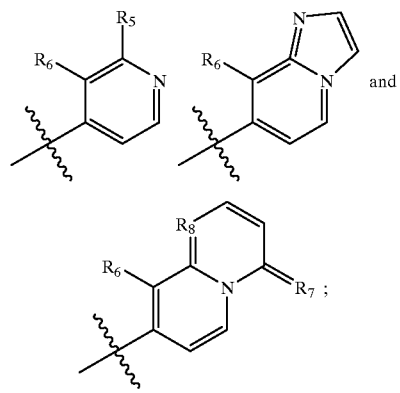

wherein
R$_4$ is a radical selected from the group consisting of alkyl, substituted alkyl, aryl and substituted aryl;
R$_5$ is a radical selected from the group consisting of —NH$_2$, —OH, —SH, —NH-alkyl, —NHR$_4$, —NH-alkylenyl-R$_4$, —O-alkyl, —O-alkylenyl-R$_4$, —S-alkyl, and —S-alkylenyl-R$_4$;
R$_6$ is a radical selected from the group consisting of —CN, —COOH, —C(O)O-alkyl, —C(O)O-alkylenyl-R$_4$, —C(O)-alkyl, —C(O)-alkylenyl-R$_4$, —C(O)-halogen, —C(O)NH$_2$, —C(O)NH-alkyl, —C(O)NH-alkylenyl-R$_4$;
R$_7$ is a radical selected from the group consisting of O, NH, and S; and
R$_8$ is N, O or S; and
R$_2$ and R$_3$ are each independently selected from the group consisting of alkyl and alkylenyl-R$_{10}$, wherein R$_{10}$ is selected from the group consisting of —OH, —OTs, halogen, spiperone, spiperone ketal, and spiperone-3-yl,
or R$_2$ and R$_3$ together form a heterocyclic ring, optionally substituted with at least one radical selected from the group consisting of alkyl, alkoxy, OH, OTs, halogen, alkyl-R$_5$, carbonyl, spiperone, spiperone ketal and spiperone-3-yl,
and further wherein one or more of the hydrogen, halogen or carbon atoms are replaced with a radiolabel; and
determining whether the structures have been labeled.
2. A method according to claim 1, wherein the compound of formula (I) is radiolabeled with $^{18}$F or $^{123}$I.

3. A method for labeling structures selected from the group consisting of β-amyloid plaques and neurofibrillary tangles in vivo, comprising:

contacting brain tissue with a compound of formula (II):

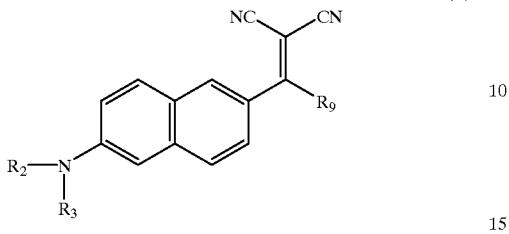

(II)

wherein
  $R_2$ and $R_3$ are each independently selected from the group consisting of alkyl and alkylenyl-$R_{10}$, wherein $R_{10}$ is selected from the group consisting of —OH, —OTs, halogen, spiperone, spiperone ketal and spiperone-3-yl,
  or $R_2$ and $R_3$ together form a heterocyclic ring, optionally substituted with at least one radical selected from the group consisting of alkyl, alkoxy, OH, OTs, halogen, alkylenyl-$R_{10}$, carbonyl, spiperone, spiperone ketal and spiperone-3-yl,
  and $R_9$ is an alkyl, aryl substituted aryl;

and further wherein one or more of the hydrogen, halogen or carbon atoms are replaced with a radiolabel; and determining whether the structures have been labeled.

4. A method according to claim 3, wherein the compound of formula (II) is radiolabeled with $^{18}$F or $^{123}$I.

5. A method according to claim 1, wherein the compound of formula (I) is 2-(1,1-dicyanopropen-2-yl)-6-dimethylaminonaphthalene containing a radiolabel.

6. A method according to claim 5, wherein the 2-(1,1-dicyanopropen-2-yl)-6-dimethylaminonaphthalene is radiolabeled with $^{18}$F or $^{123}$I.

7. A method according to claim 1, wherein the compound of formula (I) is 2-(1,1-dicyanopropen-2-yl)-6-(2-ethyl)-methylamino)-naphthalene containing a radiolabel.

8. A method according to claim 1, wherein the compound of formula (I) is 2-(1,1-dicyanopropen-2-yl)-6-(2-[$^{18}$F]-fluoroethyl)-methylamino)-naphthalene.

9. A method according to claim 1, wherein the step of determining whether the structures are labeled comprises observing the brain tissue by a method capable of detecting and depicting the distribution of the radiolabeled compound within the body.

10. A method according to claim 9, wherein the brain tissue is observed using positron emission tomography.

11. A method for diagnosing Alzheimer's disease in a patient, comprising:

injecting into brain tissue of the patient a compound of formula (I):

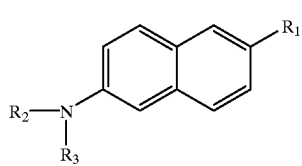

(I)

wherein:
  $R_1$ is selected from the group consisting of —C(O)-alkyl, —C(O)-alkylenyl-$R_4$, —C(O)O-alkyl, —C(O)O-alkylenyl-$R_4$, —C=C(CN)$_2$-alkyl, —C=C(CN)$_2$-alkylenyl-$R_4$,

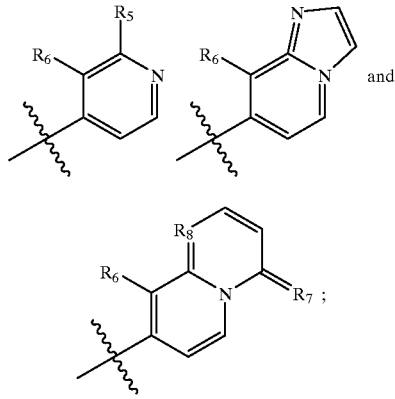

wherein
  $R_4$ is a radical selected from the group consisting of alkyl, substituted alkyl, aryl and substituted aryl;
  $R_5$ is a radical selected from the group consisting of —NH$_2$, —OH, —SH, —NH-alkyl, —NHR$_4$, —NH-alkylenyl-$R_4$, —O-alkyl, —O-alkylenyl-$R_4$, —S-alkyl, and —S-alkylenyl-$R_4$;
  $R_6$ is a radical selected from the group consisting of —CN, —COOH, —C(O)O-alkyl, —C(O)O-alkylenyl-$R_4$, —C(O)-alkyl, —C(O)-alkylenyl-$R_4$, —C(O)-halogen, —C(O)NH$_2$, —C(O)NH-alkyl, —C(O)NH-alkylenyl-$R_4$;
  $R_7$ is a radical selected from the group consisting of O, NH, and S; and
  $R_8$ is N, O or S; and
  $R_2$ and $R_3$ are each independently selected from the group consisting of alkyl and alkylenyl-$R_{10}$, wherein $R_{10}$ is selected from the group consisting of —OH, —OTs, halogen, spiperone, spiperone ketal, and spiperone-3-yl,
  or $R_2$ and $R_3$ together form a heterocyclic ring, optionally substituted with at least one radical selected from the group consisting of alkyl, alkoxy, OH, OTs, halogen, alkyl-$R_{10}$, carbonyl, spiperone, spiperone ketal and spiperone-3-yl, and further wherein one or more of the hydrogen, halogen or carbon atoms are replaced with a radiolabel; and determining whether the compound of formula (I) labeled structures selected from the group consisting of β-amyloid plaques and neurofibrillary tangles.

12. A method according to claim 11, wherein the compound of formula (I) is radiolabeled with $^{18}$F or $^{123}$I.

13. A method according to claim 11, wherein the compound of formula (I) is a compound of formula (II):

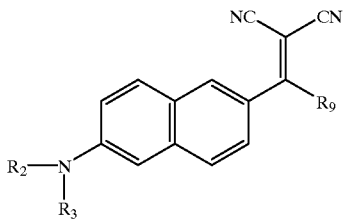

(II)

wherein $R_2$ and $R_3$ are each independently selected from the group consisting of alkyl and alkylenyl-$R_{10}$, wherein $R_{10}$ is selected from the group consisting of —OH, —OTs, halogen, spiperone, spiperone ketal and spiperone-3-yl, or $R_2$ and $R_3$ together form a heterocyclic ring, optionally substituted with at least one radical selected from the group consisting of alkyl, alkoxy, OH, OTs, halogen, alkylenyl-$R_{10}$, carbonyl, spiperone, spiperone ketal and spiperone-3-yl, and $R_9$ is an alkyl, aryl and substituted aryl.

14. A method according to claim 13, wherein the compound of formula (II) is radiolabeled with $^{18}$F or $^{123}$I.

15. A method according to claim 11, wherein the compound of formula (I) is (2-(1,1-dicyanopropen-2-yl)-6-(2-[$^{18}$F]-fluoroethyl)-methylamino)-naphthalene).

16. A method according to claim 11, wherein the determining step comprises observing the brain tissue by a method capable of detecting and depicting the distribution of the radiolabeled compound within the body.

17. A method according to claim 16, wherein the brain tissue is observed using positron emission tomography (PET).

18. A method according to claim 16, wherein the brain tissue is observed using single photon emission computed tomography (SPECT).

19. A method for labeling β-amyloid plaques, in vivo, comprising:

contacting brain tissue with a compound of formula (I):

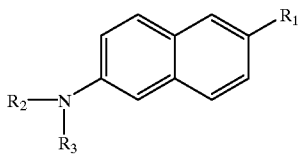

(I)

wherein:

$R_1$ is selected from the group consisting of —C(O)-alkyl, —C(O)-alkylenyl-$R_4$, —C(O)O-alkyl, —C(O)O-alkylenyl-$R_4$, —C=C(CN)$_2$-alkyl, —C=C(CN)$_2$-alkylenyl-$R_4$,

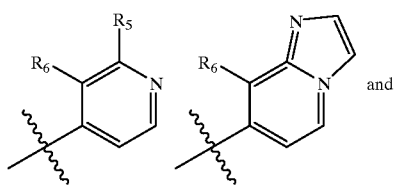

and

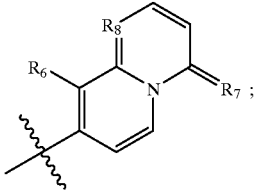

wherein $R_4$ is a radical selected from the group consisting of alkyl, substituted, alkyl, aryl and substituted aryl;

$R_5$ is a radical selected from the group consisting of —NH$_2$, —OH, —SH, —NH-alkyl, —NHR$_4$, —NH-alkylenyl-$R_4$, —O-alkyl, —O-alkylenyl-$R_4$, —S-alkyl, and —S-alkylenyl-$R_4$;

$R_6$ is a radical selected from the group consisting of —CN, —COOH, —C(O)O-alkyl, —C(O)O-alkylenyl-$R_4$, —C(O)-alkyl, —C(O)-alkylenyl-$R_4$, —C(O)-halogen, —C(O)NH$_2$, —C(O)NH-alkyl, —C(O)NH-alkylenyl-$R_4$;

$R_7$ is a radical selected from the group consisting of O, NH, and S; and $R_8$ is N, O or S; and $R_2$ and $R_3$ are each independently selected from the group consisting of alkyl and alkylenyl-$R_{10}$, wherein $R_{10}$ is selected from the group consisting of —OH, —OTs, halogen, spiperone, spiperone ketal, and spiperone-3-yl, or $R_2$ and $R_3$ together form a heterocyclic ring, optionally substituted with at least one radical selected from the group consisting of alkyl, alkoxy, OH, OTs, halogen, alkyl-$R_{10}$, carbonyl, spiperone, spiperone ketal and spiperone-3-yl, and further wherein one or more of the hydrogen, halogen or carbon atoms are replaced with a radiolabel; and determining whether the β-amyloid plaques have been labeled.

20. A method according to claim 1, wherein $R_1$ is selected from the group consisting of —C(O)—alkyl, —C(O)-alkylenyl-$R_4$, —C(O)O-alkyl, and —C(O)O-alkylenyl-$R_4$.

21. A method according to claim 1, wherein $R_2$ and $R_3$ together form a heterocyclic ring substituted with at least one radical selected from the group consisting of alkyl, alkoxy, OH, OTs, halogen, alkyl-$R_{10}$, carbonyl, spiperone, spiperone ketal and spiperone-3-yl.

22. A method according to claim 3, wherein $R_2$ and $R_3$ together form a heterocyclic ring substituted with at least one radical selected from the group consisting of alkyl, alkoxy, OH, OTs, halogen, alkyl-$R_{10}$, carbonyl, spiperone, spiperone ketal and spiperone-3-yl.

23. A method according to claim 19, wherein $R_1$ is selected from the group consisting of —C(O)-alkyl, —C(O)-alkylenyl-$R_4$, —C(O)O-alkyl, and —C(O)O-alkylenyl-$R_4$.

24. A method according to claim 19, wherein $R_2$ and $R_3$ together form a heterocyclic ring substituted with at least one radical selected from the group consisting of alkyl, alkoxy, OH, OTs, halogen, alkyl-$R_{10}$, carbonyl, spiperone, spiperone ketal and spiperone-3-yl.

25. A method according to claim 9, wherein the brain tissue is observed using single photon emission computed tomography (SPECT).

* * * * *